US008673949B2

(12) United States Patent
Albright et al.

(10) Patent No.: US 8,673,949 B2
(45) Date of Patent: Mar. 18, 2014

(54) USE OF EPOTHILONE D IN TREATING TAU-ASSOCIATED DISEASES INCLUDING ALZHEIMER'S DISEASE

(75) Inventors: Charles F. Albright, Madison, CT (US); Donna Marie Barten, West Suffield, CT (US); Francis Y. Lee, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/150,671

(22) Filed: Jun. 1, 2011

(65) Prior Publication Data

US 2011/0230528 A1 Sep. 22, 2011

Related U.S. Application Data

(63) Continuation of application No. 12/429,492, filed on Apr. 24, 2009, now abandoned.

(60) Provisional application No. 61/047,729, filed on Apr. 24, 2008.

(51) Int. Cl.
*A61K 31/365* (2006.01)
*A61K 31/427* (2006.01)
*C07D 277/22* (2006.01)

(52) U.S. Cl.
USPC ............................ 514/365; 514/450; 548/202

(58) Field of Classification Search
USPC ...................................... 514/365, 45; 548/202
See application file for complete search history.

(56) References Cited

U.S. PATENT DOCUMENTS

| 5,580,898 | A | 12/1996 | Trojanowski et al. |
| 6,242,469 | B1 | 6/2001 | Danishefsky et al. |
| 6,262,094 | B1 | 7/2001 | Hoefle et al. |
| 6,380,395 | B1 | 4/2002 | Vite et al. |
| 6,399,838 | B1 | 6/2002 | Li et al. |
| 6,498,257 | B1 | 12/2002 | Vite et al. |
| 6,605,599 | B1 | 8/2003 | Vite et al. |
| 6,800,653 | B2 | 10/2004 | Regueiro-Ren et al. |
| 6,831,090 | B2 | 12/2004 | Vite et al. |
| 7,211,593 | B2 | 5/2007 | Vite et al |
| 7,816,370 | B2 | 10/2010 | Andrieux et al. |
| 2004/0019088 | A1 | 1/2004 | Lichtner et al. |

FOREIGN PATENT DOCUMENTS

| JP | 2004-527478 T | 12/2003 |
| JP | 2007-524655 T | 7/2005 |
| WO | WO 99/02514 | 1/1999 |
| WO | WO 99/28324 | 6/1999 |
| WO | WO 00/71521 | 11/2000 |
| WO | WO 02/41691 | 5/2002 |
| WO | WO 03/074053 | 9/2003 |
| WO | WO 2004/016269 | 2/2004 |
| WO | WO 2004/087672 | 10/2004 |
| WO | WO 2005/075023 | 8/2005 |
| WO | WO 2005/105081 | 11/2005 |
| WO | WO 2006/033913 | 3/2006 |
| WO | WO 2006/009178 | 8/2006 |
| WO | WO2008/024303 A2 | 2/2008 |
| WO | WO2008/024304 A2 | 2/2008 |
| WO | WO2008/024305 A2 | 2/2008 |
| WO | WO 2009/132253 | 10/2009 |

OTHER PUBLICATIONS

Goodin et al., "Epothilones: Mechanism of Action and Biologic Activity," Journal of Clinical Oncology, 2004, vol. 22, No. 10; pp. 2015-2025.*
Document Disclosing Data (1).
Document Disclosing Data (2).
Andrieux, et al., "Microtubule Stabilizer Ameliorates Synaptic Function and Behavior in a Mouse Model for Schizophrenia", Biol. Psychiatry, vol. 60, pp. 1224-1230, 2006.
Ballatore, et al. "Paclitaxel C-10 Carbamates: Potential Candidates for the Treatment of Neurodegenerative Tauopathies", Biorganic & Medicinal Chemistry Letters, vol. 17, pp. 3642-3646, 2007.
Ballog et al., "Epothilones, a New Class of Microtubule-Stabilizing Agents with a Taxol-Like Mechanism of Action", Cancer Research, vol. 55, pp. 2325-2333, 1995.
Brunden, K.R. et al., "Epothilone D Improves Microtubule Density, Axonal Integrity, and Cognition in a Transgenic Mouse Model of Tauopathy", The Journal of Neuroscience, vol. 30, No. 41, pp. 13861-13866 (Oct. 13, 2010).
Chen, Yingzue, "Microtubule-Stabilizing Agents as a Potential Therapeutic Treatment for Alzheimer's Disease", Dissertation, Mar. 29, 2001.
Chou et al., "Desoxyepothilone B: An Efficacious Microtubule-Targeted Antitumor Agent with a Promising in Vivo Profile Relative to Epothilone B", Proc. Natl. Acad. Sci. USA, pp. 9642-9647, 1998.
Fellner et al., "Transport of Paclitaxel (Taxol) Across the Blood-Brain Barrier in Vitro and in Vivo", The Journal of Clinical Investigation, vol. 110, No. 9, pp. 1309-1318, 2002.
Goodin et al., "Epothilones: Mechanism of Action and Biologic Activity", Journal of Clinical Oncology, vol. 22, No. 10, pp. 2015-2025 (2004).
Hoffmann et al., "Sagopilone Crosses the Blood-Brain Barrier in Vivo to Inhibit Brain Tumor Growth and Metastases", Neuro-Oncology, pp. 159-166, 2009.
Kolman, "Epothilone D (Kosan/Roche)", Current Opinion in Investigational Drugs, vol. 5, No. 6, pp. 657-667, 2004.
Lace et al., "A Brief History of Tau: The Evolving View of the Microtubule-Associated Protein Tau in Neurodegenerative Diseases", Clinical Neuropathology, vol. 26, No. 2, pp. 43-58, 2007.

(Continued)

*Primary Examiner* — Sreeni Padmanabhan
*Assistant Examiner* — Jody Karol
(74) *Attorney, Agent, or Firm* — Anastasia Winslow; Pamela A. Mingo

(57) ABSTRACT

Methods of treating Tau-associated diseases, preferably tauopathies, are described using epothilone D that exhibit good brain penetration, long half-life, and high selective retention in brain, and provides effective therapies in treating tauopathies including Alzheimer's disease.

8 Claims, 11 Drawing Sheets

(56) References Cited

OTHER PUBLICATIONS

Lee et al., "Microtubule Stabilizing Drugs for the Treatment of Alzheimer's Disease", Neurobiology of Aging, vol. 15, Supplement 2, pp. S87-S89, 1994.

Zhang et al., "Microtubule-Binding Drugs Offset Tau Sequestration by Stabilizing Microtubules and Reversing Fast Axonal Transport Deficits in a Tauopathy Model", Proc. Natl. Acad. Sci. USA, vol. 102, No. 1, pp. 227-231, 2005.

Zhong, Ziyang, Declaration Under 37 CFR 1.132 dated Apr. 25, 2007, U.S. Appl. No. 10/703,404.

Andrieux, A. et al., The suppression of brain cold-stable microtubules in mice induces synaptic defects associated with neuroleptic-sensitive behavioral disorders, Genes & Development, vol. 16, pp. 2350-2364 (2002).

Nicolaou, K.C. et al., "Chemical Biology of Epothilones", Angew. Chem. Int. Ed., vol. 37, pp. 2014-2045 (1998).

European Opposition Division's Decision Revoking EP 1711230 B1 (Jan. 18, 2011).

Minutes from Oral Proceedings Before the Opposition Division (Feb. 14, 2011).

Fifre, Alexandre, et al, "Microtubule-Associated Protein MAP1A, MAP1B, and MAP2 Proteolysis During Soluble Amyloid Beta-Peptide-Induced Neuronal Apoptosis," Journal of Biological Chemistry, 281(1), pp. 229-240, 2006.

Michaelis, M.L., et al, "Protection Against Beta-Amyloid Toxicity in Primary Neurons by Paclitaxel (Taxol)," Journal of Neurochemistry, 70(4), pp. 1623-1627, 1998.

\* cited by examiner

USE OF EPOTHILONE D IN TREATING TAU-ASSOCIATED DISEASES INCLUDING ALZHEIMER'S DISEASE

CROSS-REFERENCE TO RELATED APPLICATIONS

This application is a Continuation of Non-Provisional application U.S. Ser. No. 12/429,492 filed Apr. 24, 2009 which claims the benefit of Provisional Application U.S. Ser. No. 61/047,729 filed Apr. 24, 2008.

FIELD OF THE INVENTION

This invention relates generally to the treatment of Tau-associated diseases using epothilone D, and more specifically, to the treatment of Alzheimer's Disease using epothilone D.

BACKGROUND OF THE INVENTION

Alzheimer's disease (AD) is the most common form of dementia, affecting an estimated 27 million people worldwide in 2006. Age is the greatest known risk factor for AD with an incidence of 25-50% in people aged 85 years or older. As the average age of the population increases, the number of patients with AD is expected to rise exponentially. AD is the fifth leading cause of death in people aged 65 and older, and most patients eventually need nursing home care. Consequently, AD has an enormous economic impact, e.g., estimated direct and indirect costs for 2005 in the US only were $148 billion. Besides the economic costs, AD has a devastating impact upon patients and their family members, causing severe emotional distress and turmoil.

Patients are diagnosed with probable AD based on the presence of dementia with progressive worsening of memory and other cognitive functions and with the exclusion of other causes of dementia. A diagnosis of AD can only be confirmed post-mortem as the clinical diagnosis is based on brain neuropathology, specifically, the diagnosis requires an evaluation of brain tissue, including the existence and concentration of extracellular plaques in the brain, intracellular tangles, and brain neurodegeneration. Dementia is also a required part of the diagnosis, since plaques and tangles are observed in cognitively normal adults, although usually to a lesser extent.

Two classes of medications, cholinesterase inhibitors and an N-methyl-D-aspartic acid (NMDA) antagonist, are currently approved for AD. Although these two classes of therapeutics show some clinical benefit, many patients do not respond, and these drugs only ameliorate the symptoms of AD (e.g., cognitive function) with little or no modification of disease progression. For these reasons, identification of disease-modifying therapeutics for this devastating disease is a major focus of the pharmaceutical industry.

Microtubule stabilizers have been suggested as therapies to treat tauopathies including AD. See, e.g., Lee et al. (references list, infra). In U.S. Pat. No. 5,580,898, filed May 1994 and granted Dec. 3, 1996, Trojanowski et al. suggest use of paclitaxel (TAXOL®) to treat AD patients by stabilizing microtubules. Paclitaxel has proven highly effective as a microtubule-stabilizing agent in treating cancer patients; however, it presents brain-penetration and peripheral neuropathy issues when considered for AD (further described below), and has not emerged as a viable therapy to treat AD.

In 1995, epothilone B was reported to exert microtubule-stabilizing effects similar to paclitaxel (Bollag et al. 1995). Epothilone A and epothilone B are naturally-occurring compounds that were isolated by Hofle et al. from fermentation products of the microorganism *Sorangium cellulosum* (e.g., WO 93/10121). Hofle et al. also discovered 37 natural epothilone variants and related compounds produced by *S. cellulosum* and modified strains, including epothilones C, D, E, F and other isomers and variants (e.g., U.S. Pat. No. 6,624,310).

Unique characteristics of the natural epothilones generated much interest in their exploration as potential anti-cancer drugs. Now, nearly twenty years have passed since the first discovery of the natural epothilones A and B. Hundreds of epothilone analogs have been discovered and described in various patent applications, and abundant literature has published under the rubric, "epothilones" (See, e.g., Altmann et al., references list, infra, at 396-423).

The assignee of the current application has developed ixabepilone, a semi-synthetic analog of epothilone B, for treatment of cancer. Ixabepilone has the structural formula:

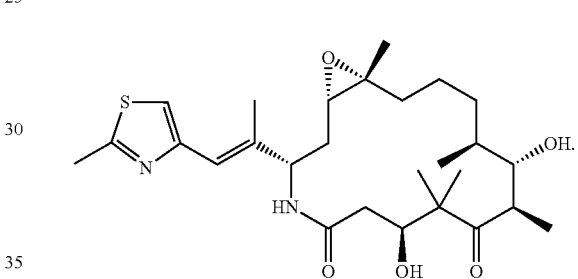

The chemical name for ixabepilone is (1S,3S,7S,10R,11S,12S,16R)-7,11-dihydroxy-8,8,10,12,16-pentamethyl-3-[(1E)-1-methyl-2-(2-methyl-4-thiazolyl)ethenyl]-17-oxa-4-azabicyclo[14.1.0]heptadecane-5,9-dione. See also U.S. Pat. No. 6,605,599, assigned to the current assignee, Bristol-Myers Squibb Company (BMS). Ixabepilone is a microtubule-stabilizing agent that has been approved by the FDA for treatment of metastatic breast cancer and is sold by BMS under the tradename IXEMPRA®. Ixabepilone can be prepared as described in U.S. Pat. No. 6,605,599 or 7,172,884, incorporated herein by reference.

Other natural epothilones and analogs are in advanced clinical trials for treatment of cancer including epothilone B (a/k/a patupilone, or EPO-906), in Phase III trials by Novartis Pharma AG, for treatment of ovarian cancer, and sagopilone (or ZK-EPO), a benzothiazolyl-7-propenyl synthetic analog of epothilone B, in Phase II trials by Bayer Schering AG for treatment of various cancers including tumors of the ovary, breast, lung, prostate and melanoma. In 2007, a Phase II trial with sagopilone was initiated in the US for treatment of brain metastases from breast cancer. Additionally, an epothilone D analog, KOS-1584, had advanced to Phase II clinical trials by Kosan Biosciences, Inc. (now a wholly-owned subsidiary of BMS) for treatment of non-small-cell lung cancer and solid tumors, and epothilone D had advanced to Phase II clinical trials for treatment of cancer by Kosan in collaboration with Hoffmann-La Roche, Inc.; however, the clinical trials with epothilone D for treating cancer were discontinued in 2007. The structure for epothilone D can be represented by the following formula:

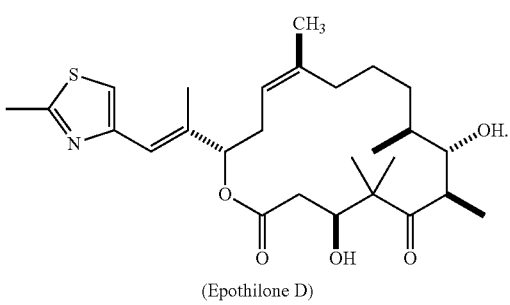

(Epothilone D)

The epothilone D compound is claimed, as composition of matter, in U.S. patent application Ser. No. 09/313,524 to Hofle et al., and described in U.S. Pat. Nos. 6,242,469 and 6,284,781 to Danishefsky et al., which application and patents were the subject of Interference No. 105,298, before the USPTO Board of Patent Appeals and Interferences.

The assignee of the current application also has clinically evaluated BMS-310705 (Compound II herein), for cancer therapy. BMS-310705 was pursued through Phase I clinical trials for treatment of ovarian cancer; it is an amino-epothilone F analog and has the chemical structure:

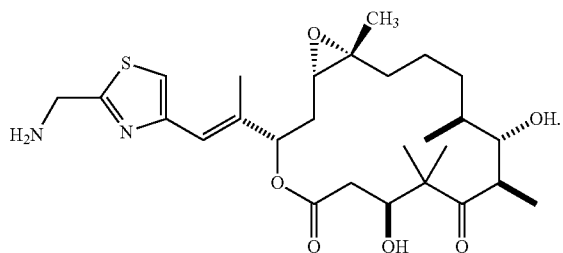 [SMILES: C/C(=C\c1csc(CN)n1)[C@@H]1C[C@@H]2O[C@]2(C)CCC[C@H](C)[C@H](O)[C@@H](C)C(=O)C(C)(C)[C@@H](O)CC(=O)O1]

Compound II (BMS 310705) can be prepared as described in U.S. Pat. No. 6,262,094, incorporated herein.

While certain of the epothilone compounds and analogs have been clinically evaluated for treating cancers, it is highly unpredictable whether a cancer drug may be effectively used to treat neurodegenerative diseases including AD. There are various factors affecting this unpredictability. One factor is the substantial difficulty of achieving good brain penetration due to the blood-brain barrier (BBB). For a compound to be useful in treating neurodegenerative brain diseases, it is necessary that the compound cross the BBB; however, since a function of the BBB is to protect the brain from external substances and toxins, discovering a useful drug that has good BBB penetration is challenging. Additionally, BBB penetration is an undesirable feature for a cancer drug (other than brain cancer drugs). With a cancer drug, BBB penetration is usually sought to be avoided, whereas for a drug designed to treat AD or other neurodegenerative brain diseases, good BBB penetration is necessary for the compound to be effective. Thus, for example, while paclitaxel is a highly-successful cancer drug, it has not emerged as a useful therapy to treat brain diseases such as AD, as it has a low rate of brain penetration through the BBB.

Further factors affecting the unpredictability of evaluating the usefulness of cancer drugs, particularly microtubule-stabilizing drugs, in treating AD and other brain diseases involve the ability of a drug to penetrate the brain, to be retained in the brain for long periods, and to selectively accumulate in the brain relative to peripheral tissues. These parameters can be measured using brain-to plasma ratios, brain half-life, and the ratio of the amount of drug retained in the brain as compared with peripheral tissues (most particularly the liver). Additionally, measuring brain penetration, retention and selective brain accumulation with microtubule-stabilizers is complex because these compounds are typically rapidly cleared from plasma but more slowly cleared from microtubule-containing tissues, making it important to set appropriate time windows for comparisons of plasma and tissue levels. The brain-to-peripheral-tissue ratio is a particularly important measurement given that microtubule-stabilizing agents at certain doses are highly cytotoxic to peripheral tissues: when microtubule-stabilizing agents, such as paclitaxel, are administered at chemotherapeutic doses, a peripheral neuropathy and other side effects often occur (Postma et al. 1999). These side effects may be tolerable in treating cancer patients but a different therapeutic window and acceptable side-effect profile exists in treating patients suffering from AD and other brain diseases.

Yet further challenges involved with looking to cancer drugs for potential application to neurodegenerative diseases involve the mode of administration and the bioavailability and cytotoxicity associated therewith.

In WO 2005/075023 A1, published Jan. 30, 2004, to Andrieux et al. of INSERM, it is suggested that certain epothilones and analogs including epothilone A, B, C, D, E, and F, and benzothiazolyl and pyridyl epothilone B and D analogs may be useful in treating diseases involving a neuronal connectivity defect, such as schizophrenia or autism. However, Andrieux et al. disclaimed and thereby taught against use of these compounds for treating AD, stating that diseases associated with neuronal connectivity defects (i.e., those claimed in that application) "are different from progressive dementing disorders like Alzheimer, which involve neuronal degeneration."

In WO 03/074053 ('053), to Lichtner et al. of Schering AG (published Sep. 12, 2003), there is a broad claim to use of a broad genus of epothilone compounds and synthetic analogs for treating brain cancer and other brain diseases, including primary brain tumor, secondary brain tumor, multiple sclerosis, and AD. Lichtner et al. report certain data on four compounds, namely, paclitaxel as compared with the compounds named therein as compound 1: 4,8-dihydroxy-16-(1-methyl-2-(2-methyl-4-thiazolyl)-ethenyl)-1-oxa-7-(1-propyl)-5,5,9,13-tetramethyl-cyclohexadec-13-ene-2,6-dione; compound 2: dihydroxy-3-(1-methyl-2-(2-methyl-4-thiazolyl)-ethenyl)-10-propyl-8,8,12,16-tetramethyl-4,17-dioxabicyclo[14.1.0]heptadecane-5,9-dione; and compound 3: 7,11-dihydroxy-3-(2-methylbenzothioazol-5-yl)-10-(prop-2-en-1-yl)-8,8,12,16-tetramethyl-4,17-diooxabicyclo[14.1.0] heptadecane-5,9-dione (see WO '053 publication at page 21).

Notably, Lichtner et al. report brain and plasma concentration data for the above three epothilone analogs, but only for periods of up to 40 minutes. Lichtner et al. are not able to report comparative data against paclitaxel on brain-to-plasma levels because their paclitaxel brain levels were below the level of detection, and they do not report data relating to brain-to-liver ratios, half-life, or brain retention for any of the compounds (e.g., concentration of drug in brain tissue over extended periods of time).

In view of the foregoing, there remains a need in the art for methods of treating tauopathies, particularly Alzheimer's disease.

SUMMARY OF THE INVENTION

The present inventors have discovered based on multiple in vivo studies including behavioral and neuropathological studies, that epothilone D achieves a surprisingly advantageous profile in treating Tau-associated diseases, including AD. The inventors have discovered that epothilone D exhibits a remarkable combination of advantageous properties, making the compound particularly well-suited to treat such diseases. These properties include not only a high level of brain penetration across the BBB, but also a surprisingly long half-life in the brain and a surprisingly high selective retention rate in the brain as compared with drug levels found in peripheral tissues, most notably, the liver, over extended periods of time. Additionally, the inventors have further discovered that surprising, therapeutic advantages in treating Tau-associated diseases, particularly, AD, can be achieved with low dosages of epothilone D, e.g., with dosages that are approximately 100-fold less than those administered to achieve chemotherapeutic effects. Consequently, the inventors have discovered methods that allow for therapies in treating Tau-associated diseases with epothilone D, particularly treatment of AD, without causing drug-induced side effects and/or drug-plasma concentration levels that would require use of the epothilone D to be discontinued. Given the low dose as compared with chemotherapeutic treatments, any side effects are greatly reduced as compared with side effects that are induced upon administration of the epothilones and analogs for treatment of cancer.

The present invention provides methods of treating Tau-associated diseases including tauopathies, using epothilone D that exhibit a surprisingly advantageous therapeutic profile, and particularly, a method of treating Alzheimer's disease comprising the step of administering a therapeutically effective amount of epothilone D to a patient.

The present invention further provides a pharmaceutical composition comprising epothilone D for treating Tau-associated diseases in a patient, wherein the composition exhibits a treatment profile comprising good brain penetrance, long half-life in the brain, and selective brain retention (e.g., high brain-to-liver ratio), as defined herein. Preferred embodiments comprise pharmaceutical compositions for treating tauopathies, particularly, AD, comprising a therapeutically-effective amount of epothilone D and a pharmaceutically acceptable carrier. Further embodiments and aspects of the invention are set forth below.

Representative sections from 3 mice per group are shown. AT8 positive staining is dark grey and black.

Figure 7A:
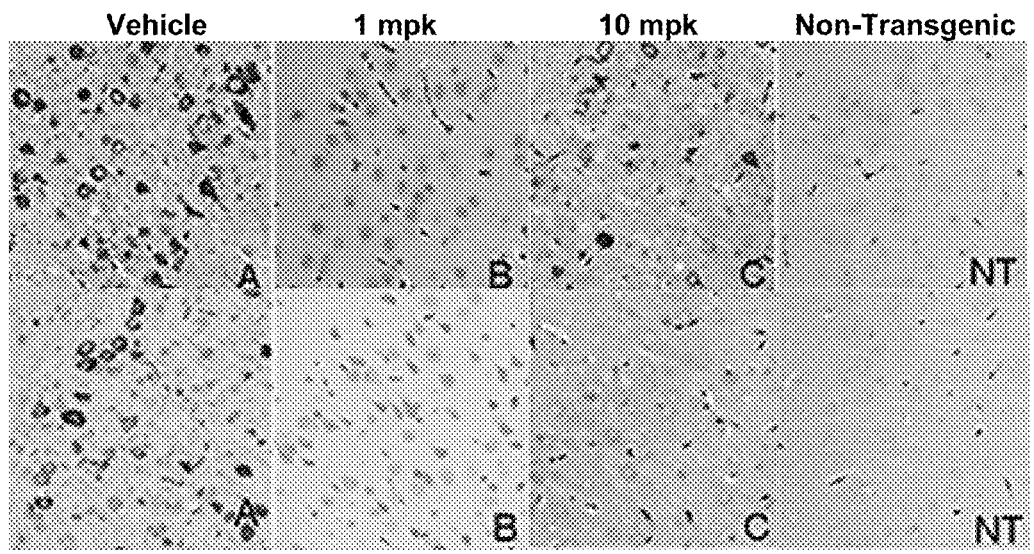
Figure 7B:
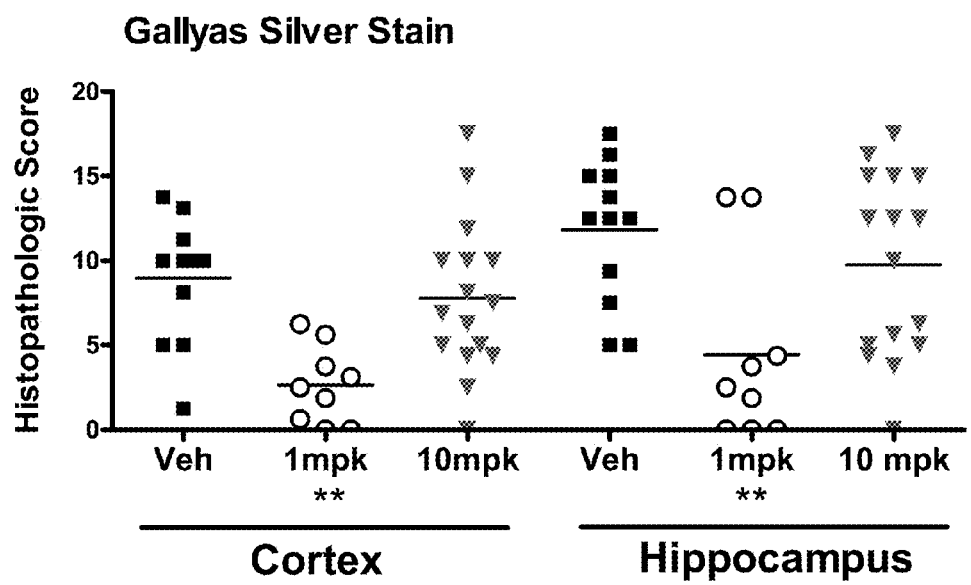

FIGS. 7A-7B show Gallyas silver staining for neurofibrillary tangles in Tg4510 mice treated with vehicle, 1 mpk epothilone D (Compound I), or 10 mpk epothilone D (Compound I). FIG. 7A shows representative micrographs of cortical staining, where the black silver stain is positive. Lighter background staining and some staining of blood vessels were observed in non-transgenic mice. FIG. 7B shows the quantitation of the silver stain in both cortex and hippocampus.

FIGS. 8A-8D show the concentration of Compound II (FIG. 8A), ixabepilone (FIG. 8B), paclitaxel (FIG. 8C) and epothilone D (Compound I) (FIG. 8D) in the plasma, brain, and liver of mice following intravenous administration at various intervals of up to 24 hours.

Figure 9:
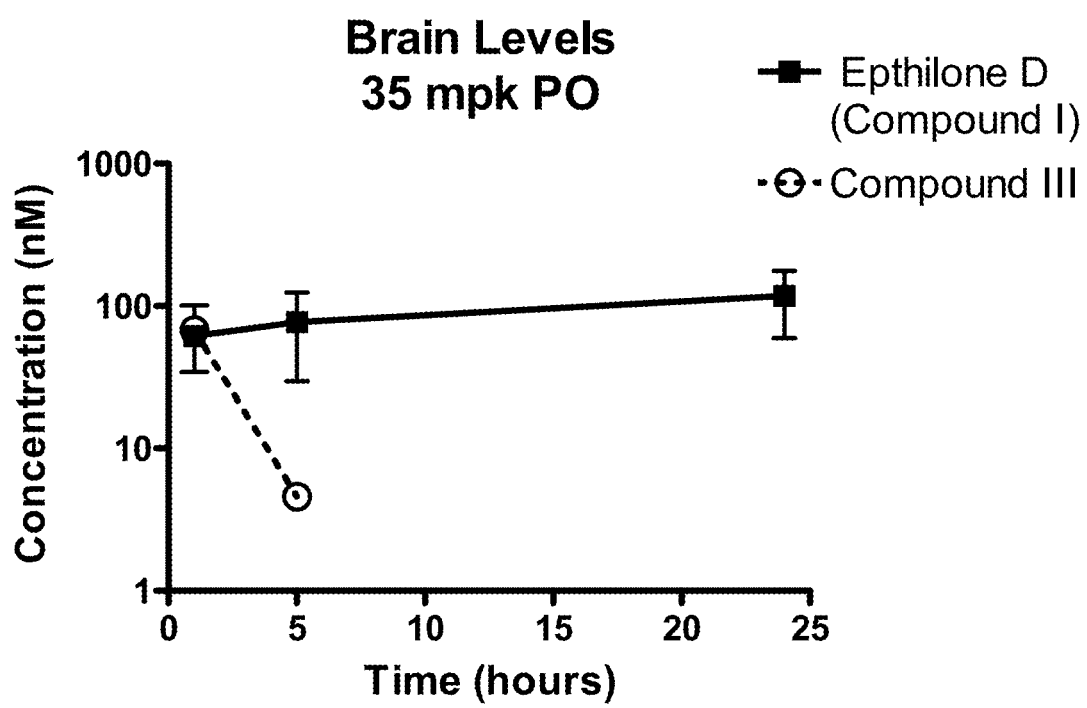

FIG. 9 shows the concentration of epothilone D (Compound 1) and Compound III (as described in Example 7 herein) in the brain after oral administration (35 mpk) up to 5 to 24 hours after dosing.

Figure 10:
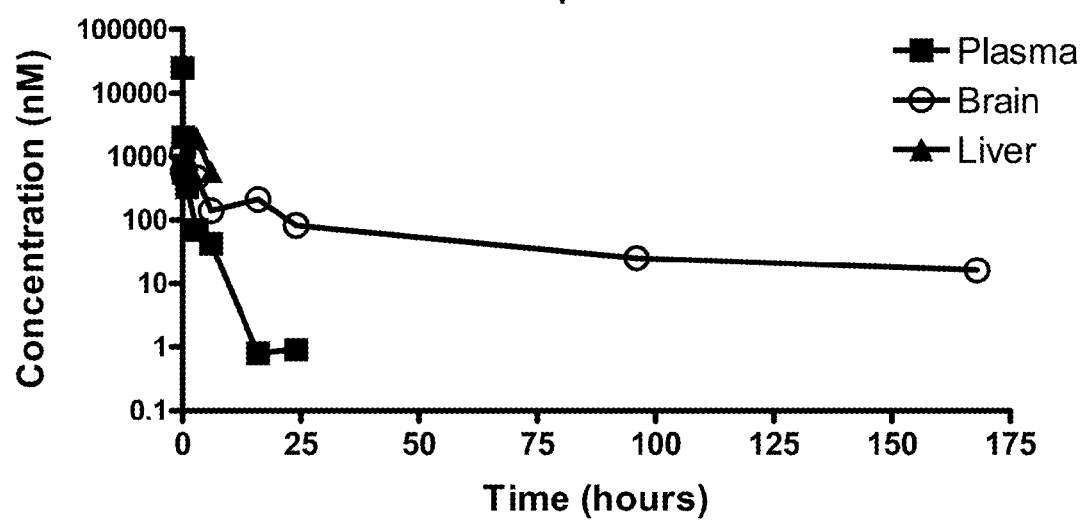

FIG. 10 shows the concentration of epothilone D in the plasma, brain and liver in mice after time intervals up to one week after dosing.

ABBREVIATIONS

The following are abbreviations of various terms used in this specification:
3R=three repeats
4R=four repeats
AD=Alzheimer's disease
APP=β-amyloid precursor protein
BBB=blood-brain barrier
BMS=Bristol-Myers Squibb, Co.
$CHCl_3$=chloroform
$CH_2Cl_2$=methylene chloride
DMAP=4-dimethylaminopyridine
EtOAc=ethyl acetate
HPLC=high pressure liquid chromatography
FDA=US Food and Drug Administration
FTDP-17=frontotemporal dementia with Parkinsonism linked to chromosome 17
H, h, hr=hour/hours
IP=intraperitoneal
IV=intravenous
LDA=lithium diisopropylamide
LLQ=lower limit of quantification
<LLQ=below LLQ, not detectable
MAP=microtubule-associated protein
MeOH=methanol
min=minutes
MTs=microtubules
mpk=milligram per kilogram
MWM=Morris water maze
nM=nanomolar
NQ=not quantifiable due to one or more datapoints<LLQ
PEG=polyethylene glycol
PGP=P-glycoprotein
PO=per os (oral administration)
PVP=polyvinylpyrrolidone
RT=room temperature
$SiO_2$=silica gel
TBAF=tetrabutylammoniumfluoride
TBS=Tris buffered saline
TEA=triethylamine
TFA=trifluoroacetic acid
THF=tetrahydrofuran
TPGS=d-α-Tocopheryl polythlene glycol 1000 succinate

DETAILED DESCRIPTION OF THE INVENTION

Definitions

"About" or "approximately" as used herein means within an acceptable range of standard deviation for the particular value as determined by one of ordinary skill in the art, considering the measurement in question and the instrument used to make the measurement (i.e., the limitations of the measurement system). For example, "about" can mean within one or more standard deviations. As applied to formulations and dosages, "about" can mean a deviation within 10%, more preferably within 5%, and even more preferably, within 2%, of the numbers reported.

The terms "at least x" and "x or more", or "x or greater", wherein x denotes a numerical value, are used interchangeably herein as they are intended to have the same meaning.

"Brain penetrance" refers to the ability of a compound to cross the BBB. Because of the rapid peripheral clearance for most microtubule stabilizing agents, it is important to measure brain-to-plasma ratios at relatively short times post-dosing, e.g., at periods of about of 20 min to 1 h post-dosing, to assess brain penetrance itself. A compound having good brain penetrance as defined herein means a compound which at 20 min to 1 h post-dosing will show a brain-to-plasma ratio of 0.5 or greater, more preferably, 0.8 or greater, and most preferably, a ratio of 1 or more (again, at a time between 20 min and 1 h post-dosing). In assessing whether a compound or drug satisfies this standard of high brain/plasma ratio (e.g., as recited in the claims herein), in vivo non-human studies must be relied upon as human brain tissue cannot be analyzed to assess drug concentration.

"Cognitive benefits" means that an improvement or lessening in decline of cognitive function for at least one patient in need of treatment is observed or reported, as characterized by cognition tests, measures of global function, and activities of daily living and behavior. Typically, cognitive benefits are measured with cognition tests designed to measure cognitive decline in a patient or group of patients. Examples of such tests include cognition tests like ADAS-cog (Alzheimer's disease Assessment Scale, cognitive subscale) and the MMSE (Mini-mental state exam); behavior tests like the NPI (Neuropsyciatric Inventory); daily living activity tests like the ADCS-ADL (Alzheimer's Disease Cooperative Study-Activities of Daily Living); and global function tests such as the CIBIC-plus (Clinician Interview Based Impression of Change), and CDR sum of boxes (Clinical Dementia Rating).

"Extended periods of time" as used herein means period of 24 hours or more, typically 24 to 76 h.

"High selective retention rate" or "high selective retention" as used herein means that the drug or compound is retained in one tissue or organ, specifically the brain, at a much higher level than is found in other tissues and organs, especially the liver, as measured at an extended period of time post-dosing. More particularly as defined herein, a high selective retention rate means the concentration of drug in the brain is 4 or more times that found in the liver at 24 or more h post-dosing, more preferably, a factor of at least 6 or more, and most preferably, at a factor of at least 8 or more at 24 h or more h post-dosing. In assessing whether a compound or drug satisfies this standard of high selective retention (e.g., as recited in the claims herein), naturally non-human studies must be relied upon as human brain tissue cannot be analyzed to assess drug concentration.

"Impact on underlying disease" means an improvement in a measure of the biomarkers and other parameters associated with the disease process, including biochemical markers in CSF or plasma, changes in brain volume, changes in brain function as measured by functional imaging, and changes in histopathology or biochemistry that might be observed after autopsy. Typical biomarkers that may be used for AD clinical trials include analytes measured in CSF such as Tau, phosphoTau, beta-amyloid, and isoprostanes, as well as brain imaging modalities such as fluorodeoxyglucose PET and volumeteric MRI. Additional biomarkers that potentially may be useful, particularly those examining synaptic activity, MT integrity/function, and oxidative stress include, but are not limited to: GABA, neuropeptide Y, alpha-synuclein, neurogranin and vasoactive intestinal peptide, tubulin, Tau fragments, ubiquitinated proteins, soluble forms of amyloid precursor protein, chromogranin B, 4-hydroxy nonenal, nitrotyrosine, and 8-hydroxy-deoxyguanidine.

"Intermittent" when used with reference to a dosing schedule means that there are breaks in the dosing schedule that are irregular. For example, a daily, weekly, biweekly, or monthly dosing schedule is not considered intermittent under this definition, because the break between doses is in each instance regular and defined by the dose cycle of administering the drug. However, a more elaborate dosing schedule with one or more irregular breaks would be considered intermittent, such as 5 days on, followed by 2 days off; or a dose administered on days 1, 8 and 15, of a 30 day cycle, and so forth.

"Long half-life", or "long brain half-life" as used herein means that a drug has a half-life of 20 or more h post-dosing (which is considered dose-independent), and more preferably, for a period 30 or more h post-dosing, and most preferably, for a period of 40 or more h post-dosing. As with the selective retention rates, in vivo non-human studies must be relied upon in assessing whether the compound has a long brain half-life.

"Low dose" as used herein means a dose of the epothilone D compound that is significantly less than that administered to achieve chemotherapeutic effects (e.g., given a particular mode of administration, clinical trial, and/or experiment), preferably a dose that is 10-fold or less than the chemotherapeutic dose, more preferably a dose that is 50-fold or more less, and even more preferably a dose that is 100-fold or more fold less than the chemotherapeutic dose, i.e., that previously assessed as chemotherapeutically effective using the same administrative method for the given experiment, study or trial. For example, in Phase II clinical trials of epothilone D, a dose administered was 100 mg/m$^2$ administered as a 90 min. infusion once a week for three weeks every four weeks (3 weeks on, 1 week off), for a cumulative total of 300 mg/m$^2$ administered every 4 weeks. A low dose relative to this clinical trial dose, as defined herein, would mean a cumulative one-month dose following IV administration of 30 mg/m$^2$ or less, more preferably a dose of 6 mg/m$^2$ or less, and even more preferably a dose of 3 mg/m$^2$ or less. Thus, as an alternative example, a low dose as compared with the above clinical trial dose when administered once every 4 weeks would be a dose of 30 mg/m$^2$, more preferably a dose of 6 mg/m$^2$, and even more preferably a dose of 3 mg/m$^2$. Since bioavailability may change depending upon the mode of administration (e.g., oral v. IV administration, with less bioavailability achieved upon oral administration), the relative dosages (i.e., assessment whether a given dose is a "low dose" as defined herein), should be based on a comparison involving the same or similar modes of administration.

"Patient in need of treatment" as used herein is intended to include use of epothilone D for a patient 1) already diagnosed with a Tau-associated disease (including a tauopathy, particularly AD) at any clinical stage, including patients having mild cognitive impairment to advanced dementia; and/or 2) who has early or prodromal symptoms and signs of a Tau-associated disease (including a tauopathy, particularly AD); and/or 3) who has been diagnosed as susceptible to a Tau-associated disease (including a tauopathy, particularly AD), due to age, hereditary, or other factors for whom a course of treatment is medically recommended to delay the onset or evolution or aggravation or deterioration of the symptoms or signs of disease.

"Statistically significant cognitive benefits" means that there are cognitive benefits (e.g., improvement or the lessening in decline of cognitive function), following a period of 6 months to a year of treatment for at least 10% or more of patients evaluated, more preferably at least 25% or more patients, and even more preferably, 50% or more of the patient group. Preferably, improvement at a rate as compared with a control group is assessed and reflects an at least 10% improvement (e.g., as evaluated based on comparative test scores between placebo and control, wherein "improvement" is intended to include reduction in decline in a patient's condition), more preferably, improvement at a rate of more than 25% or more is observed, and most preferably, at a rate of 35% or more.

"Tau-associated disease" as defined herein means diseases associated with abnormalities in Tau as well as diseases that are "tauopathies." Tau-associated diseases include, but are not limited to, frontotemporal dementia, including the subtype of frontotemporal dementia and Parkinsonism linked to chromosome 17 (FTDP-17), progressive supranuclear palsy, corticobasal degeneration, Pick's disease, agyrophilic grain disease, as well as Parkinson's disease, Down syndrome, post-encephalic Parkinsonism, myotonic dystrophy, Niemann-Pick C disease, dementia pugilistica, Blint disease, prion diseases, amyotrophic lateral sclerosis, Parkinsonism-dementia complex of Guam, multiple sclerosis, glaucoma, diabetic retinopathy, and traumatic brain injury; as well as Huntington's disease, Lewy body dementia, Charcot-Marie-Tooth disease, hereditary spastic paraplegia, and multiple system atrophy.

"Tauopathy" as defined herein means a neurodegenerative disease associated with fibrillar forms of Tau protein (tangles) in brain. These diseases include AD; however, other tauopathies include, but are not limited to, frontotemporal dementia, including the subtype of frontotemporal dementia and Parkinsonism linked to chromosome 17 (FTDP-17), progressive supranuclear palsy, corticobasal degeneration, Pick's disease, and agyrophilic grain disease.

"Therapeutically-effective amount of epothilone D" is meant an amount of epothilone D sufficient to:
(1) relieve or alleviate at least one symptom of a Tau-associated disease (preferably, a tauopathy, and more preferably, AD), including cognitive functions such as dementia, memory loss, reduced comprehension, dexterity in performing daily living activities, and/or centrally-mediated effects such as motor deficits and vision; and/or
(2) reverse, reduce, prevent, inhibit, or delay the onset or aggravation of the loss of cognitive function associated with a Tau-associated disease (preferably, a tauopathy, and more preferably, AD), and/or reverse, reduce, prevent, inhibit, or delay the onset or aggravation of one or more centrally mediated effects of said disease, including motor deficits, vision, and so on. In preferred embodiments of the invention, the epothilone D pharmaceutical compound is therapeutically effective in not only relieving or alleviating the symptoms of the Tau-associated disease (preferably, a tauopathy and more preferably, AD), but also is effective in having an impact on underlying disease (i.e., as defined above).

Alternative Embodiments of the Invention

The present inventors have found that epothilone D, administered for the treatment of a Tau-associated disease achieves a surprising level of brain penetration, long brain half-life, and selective retention, particularly as compared with other microtubule stabilizers. The inventors further have discovered that remarkably, increased therapeutic effects in treating Tau-associated diseases (particularly tauopathies, and more particularly, AD), are achieved with low doses of epothilone D. As such, a relatively low dosage of epothilone D can be administered for effective treatment of a Tau-associated disease, preferably AD. The inventors have thus developed a method of treating Alzheimer's disease employing the administration of epothilone D to a patient having AD. The method is expected to be therapeutically effective in treating AD in human patients while also posing significantly less serious or fewer side effects as compared with the side effects that typically occur when microtubule stabilizers are administered to human patients for chemotherapy. Such side effects that are reduced or eliminated may include one or more of gastrointestinal distress (including, without limitation, nausea, diarrhea, stomatitis/mucositis, vomiting, anorexia, constipation, and/or abdominal pain), liver toxicity, neutropenia, leucopenia, myelosuppression, alopecia, myalgia/arthralgia, fatigue, musculoskeletal pain, nail disorder, pyrexia, headache, skin exfoliation, and/or neurosensory effects at various grade levels.

According to an alternative embodiment of the invention, there is provided a method of treating Alzheimer's disease comprising the step of administering a therapeutically effective amount of epothilone D to a patient, wherein the epothilone D compound has two or more properties selected from good brain penetrance, a long brain half-life, and a high selective retention rate, as defined herein, more preferably, where the epothilone D demonstrates all three properties of good brain penetrance, long brain half-life, and a selective retention rate, as these terms are defined herein.

According to another embodiment of the invention, there is provided a method of treating Alzheimer's disease comprising the step of administering a therapeutically effective amount of epothilone D to a patient, wherein the epothilone D compound upon administration has properties selected from two or more of:
brain penetrance of 0.5 or greater, more preferably, 0.8 or greater, most preferably, 1 or greater, as measured at 20 min. to 1 h post-dosing; and/or
a brain half-life of at least 24 h, and more preferably, of at least 30 h, and most preferably of up to 40 h or more; and/or
a brain-liver selective retention rate of at least 4 at 24 h or more post-dosing, more preferably at a rate of 6 or more at 24 h or more, and most preferably, at a factor of 8 or more at 24 or more h post-dosing.

According to another embodiment of the invention, there is provided a method of treating Alzheimer's disease comprising the step of administering a therapeutically effective amount of epothilone D to a patient, wherein the epothilone D compound upon administration has properties selected from all three of:
brain penetrance of 0.5 or greater, more preferably, 0.8 or greater, most preferably, 1 or greater, as measured at 20 min. to 1 h post-dosing; and/or
a brain half-life of at least 24 h, and more preferably, of at least 30 h, and most preferably of up to 40 h or more; and/or a brain-liver selective retention rate of at least 4 at 24 h or more post-dosing, more preferably, at a rate of 6 or more at 24 h or more, and most preferably at a factor of 8 or more at 24 or more h post-dosing.

According to another embodiment of the invention, there is provided a method of treating Alzheimer's disease comprising the step of administering a therapeutically effective amount of epothilone D to a patient, wherein the method is therapeutically effective in treating AD in the patient without causing drug-induced side effects and/or drug-plasma concentration levels that would require use of said method to be discontinued.

According to another embodiment of the invention, there is provided a method of treating Alzheimer's disease comprising the step of administering a therapeutically effective amount of epothilone D to a patient, wherein the method provides cognitive benefits, more preferably, statistically-significant cognitive benefits, in treating AD, without causing drug-induced side effects and/or drug-plasma concentration levels that would require use of said method to be discontinued.

According to another embodiment of the invention, there is provided a method of treating Alzheimer's disease comprising the step of administering a therapeutically effective amount of epothilone D to a patient, wherein the method has an impact on underlying disease, more preferably, a statistically-significant impact on underlying disease, without causing drug-induced side effects and/or drug-plasma concentration levels that would require use of said method to be discontinued.

According to another embodiment of the invention, there is provided a method of treating Alzheimer's disease comprising the step of administering a therapeutically effective amount of epothilone D to a patient, wherein method has an impact on underlying diseases, provides cognitive benefits, and/or is otherwise therapeutically effective, without causing side effects such as gastrointestinal side effects, leucopenia, and/or neurotoxicity, that would require use of said method to be discontinued.

According to another embodiment of the invention, there is provided a method of treating Alzheimer's disease comprising the step of administering a therapeutically effective amount of epothilone D to a patient, wherein the dose of epothilone D is a low dose, as defined herein.

According to another embodiment of the invention, there is provided a method of treating Alzheimer's disease comprising the step of administering a therapeutically effective amount of epothilone D to a patient, wherein the dose of epothilone D is between 0.001-10 mg/m$^2$, or alternatively, at a dose between 0.00003-0.3 mpk, administered on a daily, weekly, or intermittent dosing cycle.

According to another embodiment of the invention, there is provided a method of treating Alzheimer's disease comprising the step of administering a therapeutically effective amount of epothilone D to a patient, wherein the epothilone D is administered via IV, and the dose of epothilone D over a cumulative monthly dosing cycle (i.e., total dosage of compound administered over a one month cycle, regardless of schedule, e.g., weekly, bi-weekly, 3 week on, 1 week off, etc.) is in the range between 0.001-5 mg/m$^2$, more preferably between 0.01-5 mg/m$^2$, even more preferably between 0.01-3 mg/m$^2$, yet even more preferably between 0.1-3 mg/m$^2$, and most preferably between 0.1-1 mg/m$^2$.

According to another embodiment of the invention, there is provided a method of treating Alzheimer's disease comprising the step of administering a therapeutically effective amount of epothilone D to a patient, wherein the epothilone D is administered orally, and the dose of epothilone D calculated on a daily basis is in the range between 0.001-2 mg/m$^2$, more preferably between 0.01-2 mg/m$^2$, even more preferably between 0.1-2 mg/m$^2$, yet even more preferably between 0.2-2 mg/m$^2$.

According to another embodiment of the invention, there is provided a method of treating Alzheimer's disease comprising the step of administering a therapeutically effective amount of epothilone D to a patient, wherein the epothilone D is administered orally, and the dose of epothilone D for a cumulative monthly basis (i.e., total dosage of compound administered over a one month cycle, regardless of schedule, e.g., daily, weekly, bi-weekly, etc.) is in the range between 0.03-60 mg/m$^2$, more preferably between 0.30-60 mg/m$^2$, even more preferably between 3-60 mg/m$^2$, yet even more preferably between 6-60 mg/m$^2$.

According to another embodiment of the invention, there is provided a method of treating Alzheimer's disease comprising the step of administering a therapeutically effective amount of epothilone D to a patient, wherein the epothilone D is administered orally on a dosing schedule selected from once daily, once weekly, once every two weeks, or once a month.

According to another embodiment of the invention, there is provided a method of treating Alzheimer's disease comprising the step of administering a therapeutically effective amount of epothilone D to a patient, wherein the epothilone D is administered orally on a dosing schedule selected from once daily, and wherein the daily dose of epothilone D is between 0.2 to 2 mg/m$^2$.

According to another aspect of the invention, there are provided methods of treating other tauopathies, besides AD, according to any one of the embodiments of the invention recited above. For example, such other tauopathies may include one or more of the diseases referenced in the definition of "tauopathy-associated disease" herein. For example, one embodiment of the invention comprises use of epothilone D, according to any of the above embodiments, to treat not only AD but also a disease selected from frontotemporal dementia, including the subtype of frontotemporal dementia and Parkinsonism linked to chromosome 17 (FTDP-17), progressive supranuclear palsy, corticobasal degeneration, Pick's disease, and agyrophilic grain disease, Parkinson's disease, Down syndrome, post-encephalic Parkinsonism, myotonic dystrophy, Niemann-Pick C disease, dementia pugilistica, Blint disease, prion diseases, amyotrophic lateral sclerosis, Parkinsonism-dementia complex of Guam, multiple sclerosis, glaucoma, diabetic retinopathy and/or traumatic brain injury. A preferred embodiment comprises use of epothilone D, according to any of the embodiments described herein, to treat a tauopathy, including, without limitation, a disease selected from AD, frontotemporal dementia, including the subtype of frontotemporal dementia and Parkinsonism linked to chromosome 17 (FTDP-17), progressive supranuclear palsy, corticobasal degeneration, Pick's disease, and agyrophilic grain disease.

According to another embodiment of the invention, there is provided epothilone D, for use in treating a Tau-associated disease, more preferably, a tauopathy, most preferably AD.

It is contemplated that each of the above inventive methods also may be combined with one or more other inventive methods, and all such various combinations of the above inventive methods are contemplated herein. For example, one combination of the above inventive methods may comprise a method of treating Alzheimer's disease comprising the step of administering a therapeutically effective amount of epothilone D to a patient, wherein the method is therapeutically effective in treating AD in the patient without causing drug-induced side effects and/or drug-plasma concentration levels that would require use of said method to be discontinued; and wherein the dose of epothilone D is a cumulative monthly dose of between 0.001-5 mg/m$^2$, administered via IV; and/or wherein the dose of epothilone D is between 0.001 to 2 mg/m$^2$, administered PO daily; and/or wherein the dose of epothilone D is selected from a dose within any one of the preferred ranges expressed above for oral or IV administration.

It also is contemplated also that any of the recited methods of treatment may by combined with the embodiment involving epothilone D, for use in treating a tauopathy, preferably AD, in a human patient. Thus, for example, one embodiment of the invention, comprising a combination of the above alternative embodiments, would comprise epothilone D for treating AD, wherein the use is therapeutically effective in treating AD, and wherein the epothilone D is administered to the patient at a dose between 0.001-10 mg/m$^2$, or alternatively, at a dose between 0.00003-0.3 mpk, administered on a daily, weekly, or intermittent dosing cycle. Yet another embodiment would comprise epothilone D, for treating a tauopathy, particularly AD, wherein the epothilone D is administered to a human patient at a low dose and is therapeutically effective in having an impact on underlying disease and/or providing cognitive benefits.

According to another embodiment of the invention, there is provided a pharmaceutical formulation comprising epothilone D suitable for administration to a human patient in need of treatment for a Tau-associated disease, preferably a tauopathy, more preferably, AD, wherein administration of the formulation is therapeutically effective in treating the disease in the patient without causing drug-induced side effects and/or drug-plasma concentration levels that would require use of said epothilone D formulation to be discontinued.

According to yet another embodiment of the invention, there is provided a pharmaceutical formulation comprising epothilone D suitable for administration to a human patient for treating a Tau-associated disease, preferably a tauopathy, more preferably AD, wherein administration of the formulation provides statistically-significant cognitive benefits in treating the disease, without causing drug-induced side effects and/or drug-plasma concentration levels that would require use of said epothilone D formulation to be discontinued.

According to yet another embodiment of the invention, there is provided a pharmaceutical formulation comprising epothilone D suitable for administration to a human patient for treating a Tau-associated disease, preferably a tauopathy, more preferably AD, wherein the formulation is effective in providing an impact on underlying disease, without causing drug-induced side effects and/or drug-plasma concentration levels that would require use of said epothilone D formulation to be discontinued.

According to yet another embodiment of the invention, there is provided a pharmaceutical formulation suitable for administration to a human patient for treating a Tau-associated disease, preferably a tauopathy, more preferably, AD, wherein the formulation comprises a dosage unit of epothilone D of between 0.0001-10 mg/m$^2$, more preferably between 0.001-5 mg/m$^2$, more preferably between 0.001-3 mg/m$^2$, even more preferably between 0.001-1 mg/m$^2$, and most preferably between 0.001-0.5 mg/m$^2$.

According to yet another embodiment of the invention, there is provided a pharmaceutical formulation for IV administration to a human patient, wherein said formulation is suitable for delivery of a cumulative monthly dose of epothilone D in the range between 0.001-5 mg/m$^2$, more preferably between 0.01-5 mg/m$^2$, even more preferably between 0.01-3 mg/m$^2$, yet even more preferably between 0.1-3 mg/m$^2$, and most preferably between 0.1-1 mg/m$^2$.

According to yet another embodiment of the invention, there is provided a pharmaceutical formulation for oral administration to a human patient, wherein said formulation is suitable for delivery of a cumulative monthly oral dose of epothilone D in the range between 0.03-60 mg/m$^2$, more preferably between 0.30-60 mg/m$^2$, even more preferably between 3-60 mg/m$^2$, yet even more preferably between 6-60 mg/m$^2$.

According to yet another embodiment of the invention, there is provided a pharmaceutical formulation for administration to a human patient, wherein said formulation comprises epothilone D in a pharmaceutically acceptable solvent system comprising from about 0 to 50% propylene glycol, about 1 to 10% TPGS, about 0.5 to 10% ethanol, about 0-90% water, and/or about 5 to 85% PEG such as PEG-400.

Combinations of each of the above inventive pharmaceutical formulations are also contemplated herein.

Utility

Tauopathies

Tauopathies are neurodegenerative diseases associated with abnormal forms of Tau protein in brain tissue. Alzheimer's Disease (AD) was the first neurodegenerative disease to be identified as implicating Tau dysfunction. In particular, neurofibrillary tangles—the presence of which is one of the hallmark pathologies in AD—were found to contain fibrillar, hyperphosphorylated, conformationally-altered forms of the Tau protein. Subsequently, other tauopathies were identified including frontotemporal dementia and Parkinsonism linked to chromosome 17 (FTDP-17), progressive supranuclear palsy, corticobasal degeneration, Pick's disease, and agyrophilic grain disease. In addition, a link with Tau abnormalities (including hyperphosphorylated Tau, Tau aggregates, and/or an association with the H1/H1 Tau haplotype) has been associated with Parkinson's disease, Down syndrome, post-encephalic Parkinsonism, myotonic dystrophy, Niemann-Pick C disease, dementia pugilistica, Blint disease, prion diseases, amyotrophic lateral sclerosis, Parkinsonism-dementia complex of Guam, multiple sclerosis, glaucoma, diabetic retinopathy and traumatic brain injury (Avila et al. 2004; Bartosik-Psujek et al. 2006; Dickey et al. 2006; Wostyn et al. 2008).

Tau is a 50 to 75 kDa microtubule-associated protein (MAP) that binds and stabilizes microtubules (MTs). There are six primary sequence variants of Tau, and these variants are formed by alternative splicing (Lace et al. 2007). The splice variants contain zero, one, or two (0N, 1N, or 2N) N-terminal inserts in combination with either three repeats (3R) or four repeats (4R) of a microtubule-binding domain. The repeat domains are necessary for microtubule stabilization, while proline-rich regions on either side of the repeat domains are necessary for binding to the microtubules (Preuss et al. 1997). The repeat domains and proline-rich regions are phosphorylated by multiple kinases, leading to dissociation of Tau from microtubules. The N-terminus of Tau extends away from the microtubule surface, where it is believed to assist in determining the spacing between microtubules and in binding of the motor protein dynactin to the microtubules (Magnani et al. 2007). In normal cells, there are roughly equal levels of 3R Tau and 4R Tau present. 4R Tau binds more tightly to microtubules than does 3R Tau.

Tau is most abundant in neurons where it is predominantly localized to axons. Tau is the major microtubule-associated protein in neuronal axons, while the MAP1 family is widely distributed in neurons, and the MAP2 family is predominantly somatodendritic. Tau stabilizes axonal microtubules, thereby facilitating transport of proteins, organelles, lipids, cellular components targeted for degradation, and cell signaling molecules bi-directionally between the cell body and the synaptic terminals. Tau dysfunction could interfere with axonal trafficking and thereby affect neuronal function and survival. The Tau gene can be knocked out in mice with mild consequences, but if both Tau and MAP 1B genes are removed, the double knockout mice die as embryos. It appears that alterations in expression of some MAPs can substitute for each other in many cases, including development (Avila et al. 2004).

In some cases, mutations in the gene encoding Tau (sometimes called MAPT) cause tauopathies, particularly in FTDP-17 and other frontotemporal dementias. Many FTDP-17 mutations decrease binding to microtubules in vitro and/or increase their propensity to form fibrils (Lace et al. 2007). Other tauopathy-associated mutations alter the splice pattern of Tau to generate predominantly 3R or 4R Tau. Yet another class of Tau mutations on the N-terminus alters the ability to bind to dynactin (Magnani et al. 2007). All of these mutations have the potential to interfere with normal functions of Tau. In the case of AD, it is thought that β-amyloid (Aβ) leads to abnormalities in Tau.

Although tangles and other Tau aggregates are a pathologic feature of tauopathies, several lines of evidence suggest that some other, soluble, unidentified form of abnormal Tau is neurotoxic. The data suggesting that Tau aggregated into neurofibrillary tangles is not directly pathogenic include observations of human brains and mouse models. For instance, examination of different regions and disease stages of Alzheimer's disease brains has led to the conclusion that neurons can survive and function with neurofibrillary tangles for decades (Morsch et al. 1999). Likewise, human Tau (hTau) transgenic mice have tangles and severe neurodegeneration, but the neurons with tangles do not show selective signs of distress and are too few in number to account for the dramatic loss in neurons observed in this model (Andorfer et al. 2005). Tg4510, an inducible Tau transgenic line, shows dramatic and rapid tangle formation, neurodegeneration, and behavioral deficits when Tau-P301L is induced (Santacruz et al., 2005). When Tau-P301L expression is repressed, neurodegeneration and cognitive deficits are greatly reduced, but tangle formation continues. Further studies using these mice show that soluble Tau multimers correlate with cognitive deficits. Similar Tau multimers are also observed in FTDP-17 and AD brain tissue (Berger et al. 2007). Finally, evidence for non-fibrillar Tau being involved in behavioral deficits in AD was obtained using transgenic mice overexpressing a mutant form of β-amyloid precursor protein (APP) (Roberson et al., 2007). When these APP mice were crossed with Tau knockout mice, amyloid plaques were formed, but behavioral deficits and synaptic abnormalities were prevented. In this APP line, Tau abnormalities could not be detected in the presence of synaptic and behavioral deficits. Taken together, these studies show that a soluble, unidentified form of abnormal Tau is likely the neurotoxic species.

Microtubule Stabilization for Treatment of Tauopathies

There are two major hypotheses for the role of Tau in neurodegenerative disease. One hypothesis posits that abnormal forms of Tau disrupt cellular function, while the other hypothesis posits that the loss of functional Tau leads to microtubule destabilization (Avila et al. 2004; Lace et al. 2007). It is based on the second hypothesis that microtubule stabilizers have been suggested as therapies to treat tauopathies (Lee et al. 1994; U.S. Pat. No. 5,580,898). Inappropriate disruptions in axonal trafficking have been implicated in a number of diseases in addition to those identified with abnormalities in Tau. These include Huntington's disease, Lewy body Dementia, Charcot-Marie-Tooth disease, hereditary spastic paraplegia, and multiple system atrophy (Roy et al. 2005).

To test if microtubule stabilizers could benefit mice that overexpress Tau, PrP T44 Tau transgenic mice were treated with paclitaxel (Zhang et al., 2005). PrP T44 mice overexpress normal human 0N3R Tau in spinal cord neurons and consequently develop motor deficits due to Tau overexpression. Paclitaxel treatment for 3 months reduced motor dysfunction and increased microtubule numbers and axonal transport in the ventral roots of the spinal cord. Although paclitaxel is poorly CNS-penetrant, it was able to influence the efferent axons from neurons in the ventral horn of the spinal cord which are outside the blood-brain barrier. Interestingly, Tau pathology in this model (spheroids) was unaffected. Since this model does not show neuronal loss, the effect of microtubule stabilizers on neuronal survival could not be assessed. Additionally, it is unclear whether the motor benefits observed in the spinal cord tauopathy would translate into cognitive benefits in a cortical-hippocampal tauopathy. For example, opposite results were observed with the cross of two different tauopathy transgenic mouse lines to transgenic mice that overexpress glycogen synthase kinase 3 (Gsk3). In the spinal cord tauopathy model, the Tau-Gsk3 bigenic animals had reduced pathology, while in the forebrain tauopathy model, the Tau-Gsk3 bigenic animals showed increased pathology (Spittaels et al. 2000; Terwel et al. 2008).

Microtubule stabilization has been offered as an explanation for the effects of NAP, a peptide of sequence NAPV-SIPQ, in several animal models. In particular, NAP has neurotrophic, anti-inflammatory, anti-apoptotic, and neuroprotective activities in many cellular and in vivo models, including middle cerebral artery occlusion (stroke model), head trauma, cholinotoxic lesions, aging, and developmental defects in fetal alcohol syndrome and apolipoprotein E deficient mice (Gozes et al. 2006; Gozes 2007). As for tauopathies, NAP administration for 3 or 6 months is reported to reduce Aβ levels, hyperphosphorylated Tau, and sarcosyl insoluble Tau while increasing soluble Tau in 3×Tg mice (Matsuoka et al. 2007; Matsuoka et al. 2008). 3×Tg mice overexpress APP and Tau-P301L (Oddo et al. 2003). The mechanism of NAP activity is not fully defined, but there is evidence, based on binding of tubulin to a NAP affinity column and effects on microtubule formation and/or stabilization in cultured neurons, that NAP binds to microtubules (Divinski et al. 2006). NAP is also known to inhibit Aβ aggregation, so it may be acting upstream of Tau in the 3×Tg model. NAP is not likely to act as a typical microtubule-stabilizing agent, as it is able to protect against paclitaxel-induced peripheral neuropathy in rats (U.S. Patent Application Publication No. 2006/0247168 A1). When microtubule-stabilizing agents, such as paclitaxel, are administered at high, chemotherapeutic doses, a peripheral neuropathy often occurs (Postma et al. 1999) that is believed to result from the over-stabilization and bundling of microtubules in peripheral nerves. Since NAP prevents paclitaxel-induced peripheral neuropathy in rats, paclitaxel and NAP are unlikely to act through identical mechanisms.

There are also suggestions that microtubule stabilizers could have neuroprotective effects unrelated to obvious Tau dysfunction. Microtubule-stabilizing compounds protect cultured neurons from multiple toxic insults, including Aβ42, oxidative stress from soluble Aβ40, lysosomal disruption, calcium-induced toxicity, and glutamate-induced toxicity (Burke et al. 1994; Furukawa 1995; Sponne et al. 2003; Michaelis et al. 2005; Butler et al. 2007). It is hypothesized that microtubules play a key role not only in transport mechanisms, but also in regulation of cell signaling, particularly calcium signaling, possibly through anchoring of macromolecular signaling complexes in the vicinity of the plasma membrane (Michaelis et al. 2005). Microtubule stabilizing agents have also been shown to enhance mitochondrial function by reducing reactive oxygen species generation and increasing expression of the oxidative phosphorylation genes involved in ATP production (Wagner et al. 2008). Microtubule-stabilizing agents are also known to broadly influence cell signaling during disruption of the mitotic spindle in cancer cells (Bergstralh et al. 2006).

Brain-Penetrant Microtubule Stabilizers

The therapeutic target of microtubule stabilizers for tauopathies and other neurodegenerative diseases is microtubules in the brain. However, microtubule stabilizers can cause toxicity to peripheral tissues, such as inhibition of cell proliferation, particularly in the gastrointestinal tract and hematopoietic cells, and peripheral neuropathy. It is thus highly desired to identify microtubule stabilizers with excellent brain penetration and selective retention in the brain as compared with peripheral tissues, so as to maximize the therapeutic index for tauopathies and other neurodegenerative diseases. The ability of compounds to bind with a longer half life to brain tissue relative to peripheral tissues is a highly desired property.

The taxane series of microtubule stabilizers are substrates of multiple multi-drug resistance transporters, such as P-glycoprotein (PGP), ATP-binding cassette, multidrug resistance protein, and breast cancer resistance protein. These multi-drug resistance transporters prevent compounds from accumulating in tumor and brain tissue. Multiple labs have worked to synthesize taxanes that are not substrates for multi-drug resistance transporters, particularly PGP, with limited success (Minderman et al. 2004; Rice et al. 2005; Ballatore et al. 2007). Co-administration of a PGP inhibitor with paclitaxel has also been attempted (Fellner et al. 2002). These efforts have shown results of some taxane entry into the brain, achieving, for example, approximately ⅓₀th the levels of paclitaxel in the brain as in the kidney with a PGP inhibitor, or brain levels in the µM range with KU-237, but only for 4 h after administration (Michaelis 2006). Hence, use of PGP inhibitors are not an attractive method to increase the brain penetration of taxanes.

Methods of Preparation and Formulations

Epothilone D is a known compound which has been chemically synthesized de novo and also has been isolated from fermentations of *Sorangium cellulosum* strains as minor products in the fermentation of *S. cellulosum*. Total synthesis of epothilone D is reported in U.S. Pat. No. 6,242,469 to Danishefsky et al., and additional methods for preparing epothilone D and other epothilone compounds can be found at U.S. Pat. Nos. 6,204,388, 6,288,237, 6,303,342; WO 03/072730, U.S. Pat. No. 6,410,301; U.S. Patent Application Publication No. 2002/0137152A1; U.S. Pat. No. 6,867,333, U.S. Patent Application Publication No. 2006/004065, each of which is incorporated herein by reference. Synthetic methods for manufacturing epothilone D have been characterized as impractical for full-scale pharmaceutical development. One alternative method of preparation is to engage in large-scale fermentation of epothilone B, for example, as described in U.S. Pat. No. 7,172,884 B2, with use of improved strains designed to provide relatively large yields of epothilone B, and the epothilone B can be de-epoxidized to provide epothilone D. Methods of de-epoxidation are well known but also can be found in U.S. Pat. No. 6,965,034 (WO 99/43653), to Danishefsky et al., particularly as applied to epothilone D.

Further methods for making epothilone D are set forth in U.S. Pat. Nos. 6,998,256 B2 and 7,067,286, "Methods of Obtaining Epothilone D using Crystallization and/or By the Culture of Cells in the Presence of Methyl Oleate," which describe the biosynthetic production of epothilone D using *Myxococcus xanthus* strains K111-40-1 and K111-72.4.4, and/or other recombinant strains that have been developed by Kosan Biosciences Inc. (now BMS), to improve production of epothilone D. Fermentation and purification conditions for making epothilone D are also set forth in U.S. Pat. Nos. 6,998,256 B2 and 7,067,286, as well as U.S. Pat. Nos. 6,583,290, 6,858,411, 6,921,650, and 7,129,071, each of which is assigned to Kosan (now BMS, the current assignee), and incorporated herein by reference. See also, Lau et al., Kosan Biosciences, "Optimizing the Heterologous Production of Epothilone D in *Myxococcus xanthus*," *Biotechnology & Bioengineering*, 78(3):280-288 (May 5, 2002).

Yet further methods that may be used in making epothilone D are illustrated in U.S. patent application Ser. No. 12/118,432. This application discloses a combination of chemical and biosynthetic steps to prepare epothilones such as epothilone D. For example, methods are provided in which one or more intermediates that may be used for epothilone synthesis are obtained through fermentation of recombinant cells, and then the biosynthesized intermediates with use of recombinant cells, disclosed therein, are converted to the final epothilone compounds via chemical synthesis.

The epothilone D used in methods of the present invention can be administered to a patient in various ways known in the art, typically by intravenous (IV) administration, subcutaneous administration, oral administration, and so on. For example, epothilone D can be formulated with a pharmaceutically acceptable vehicle or diluent. A pharmaceutical composition comprising epothilone D can be formulated in a classical manner using solid or liquid vehicles, diluents, and additives appropriate to the desired mode of administration.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution (0.9% Sodium Chloride Injection [Normal Saline] or 5% Dextrose Injection), or other suitable dispersing or wetting and suspending agents, including synthetic mono- or diglycerides, and fatty acids. Pharmaceutically acceptable compositions and/or methods of administering compounds of the invention may include use of co-solvents including, but not limited to ethanol, N,N dimethylacetamide, propylene glycol, glycerol and polyethylene glycols, e.g., polyethylene glycol 300 and/or polyethylene glycol 400. Surfactants (pharmaceutically-acceptable surface active agent) may be used to increase a compound's spreading or wetting properties by reducing its surface tension, including without limitation, d-α-Tocopheryl polyethylene glycol 1000 succinate (TPGS), Cremophor, Solutol HS 15, polysorbate 80, polysorbate 20, poloxamer, pyrrolidones such as N-alkylpyrrolidone (e.g., N-methylpyrrolidone) and/or polyvinylpyrrolidone; however, use of Cremophor has disadvantages and is not preferred. The formulation may also comprise use of one or more "buffers" (e.g., an ingredient which imparts an ability to resist change in the effective acidity or alkalinity of a medium upon the addition of increments of an acid or base), including, without limitation, sodium phosphate, sodium citrate, diethanolamine, triethanolamine, L-arginine, L-lysine, L-histidine, L-alanine, glycine, sodium carbonate, tromethamine (a/k/a tris[hydroxymethyl]aminomethane or Tris), and/or mixtures thereof.

Formulations for administering epothilone compounds, including formulations that avoid use of non-ionic surfactants such as Cremophor, are described in the prior art. For example, a formulation for use in IV administration that comprises a mixture of propylene glycol and ethanol is described in U.S. Pat. No. 6,683,100. Further formulations may comprise mixtures of polyethylene glycol/dehydrated alcohol, or propylene glycol or glycerol/dehydrated alcohol. For example, WO 2006/105399 (PCT/US2006/011920) to BMS, discloses formulations that include mixtures of about 30 to 70 percent by volume dehydrated alcohol for each 30 to 70 percent by volume PEG 300 and/or PEG 400, which can be diluted with saline or dextrose infusion fluids for IV administration, and may be applied for use in administering epothilone D to patients via IV administration. In such formulations, it is preferred that the amount of ethanol be minimized to avoid side effects associated with ethanol administration. Optimal ratios of solvents may be readily obtained by one skilled in the field.

Further preferred formulations specifically designed for administering epothilone D and analogs are disclosed in U.S. Pat. No. 7,091,193 (also published as U.S. Patent Application Publication No. 2005/0148543), to Kosan (now BMS). This patent describes a formulation wherein epothilone D and a hydroxypropyl-beta-cyclodextrin are combined in an alcohol-water solution that is then lyophilized. Embodiments involve use of about 10 mg epothilone D and about 0.4 g of hydroxypropyl-beta-cyclodextrin combined in a 60% tert-butanol-water solution that is then lyophilized (ingredients can be reduced proportionately for preparation of individual, lower dosages units, according to the current invention). The lyophilized active ingredient "cake" can then be reconstituted for IV administration with use of water, ethanol, and/or glycol, which may include propylene glycol, polyethylene glycol 400, polyoxyethylene sorbitan monooleate (sold under the trade name TWEEN 80), and related oxygenated hydrocarbons. It is understood that glycols of various chain lengths and molecular weights (e.g., polyethylene glycol 1000, other TWEEN compounds) may be used.

As a more specific example, a formulation that may be used to deliver epothilone D to a patient according to the invention may comprise about 0 to 50% propylene glycol, about 1 to 10% TPGS, about 0.5 to 10% ethanol, about 0-90% water, and/or about 5 to 85% PEG such as PEG-400. More specifically, a formulation may comprise:
50% propylene glycol, 10% TPGS, 10% ethanol, 30% water; or
10% propylene glycol, 40% PEG-400, 5% TPGS, 5% ethanol, 40% water; or
85% PEG-400, 10% TPGS, 5% ethanol; or
8.5% PEG-400, 1% TPGS, 0.5% ethanol, 90% water.

One preferred method of administering epothilone D according to the invention involves oral administration. U.S. Pat. No. 6,576,651 discloses methods for oral administration of epothilones with use of one or more pharmaceutically acceptable acid-neutralizing buffers. However, a preferred method of administration would involve use of a tablet or capsule, including a solid tablet or capsule or fluid or gelatin-filled capsule. A solid tablet or capsule of epothilone D may be prepared with one or more enteric coatings. Enteric coatings have been used for many years to arrest the release of the drug from orally ingestible dosage forms. Depending upon the composition and/or thickness, the enteric coatings are resistant to stomach acid for required periods of time before they begin to disintegrate and permit slow release of the drug in the lower stomach or upper part of the small intestines. Examples of some enteric coatings are disclosed in U.S. Pat. Nos. 6,224,910, 5,225,202, 2,809,918, 3,835,221, 4,728,512 and 4,794,001, each of which is incorporated herein by reference.

An enteric coated tablet directed to use of epothilone D is described in U.S. patent application Ser. No. 11/281,834, incorporated herein by reference, which may be used to formulate tablets of capsules of epothilone to practice the invention. This formulation involves use of an inactive base particle, such as a sugar bead, to which the active ingredient (i.e., epothilone D), is applied, which is then encapsulated by an enteric coating polymer, and/or one or more subcoat layers. The beads are then included within a capsule. Enteric coatings for use in formulating epothilone D tablets or capsules may include enteric coating polymers, such as, for example, hydroxypropyl methylcellulose phthalate, polyvinyl acetate phthalate, cellulose acetate phthalate, acrylic acid copolymers, and methacrylic acid copolymers. One example of a methacrylic acid copolymer that may be used to form an enteric coating is EUDRAGIT® L-30-D 55 aqueous copolymer dispersion, which comprises an anionic copolymer derived from methacrylic acid and ethyl acrylate with a ratio of free carboxyl groups to the ethyl ester groups of approximately 1:1, and a mean molecular weight of approximately 250,000, which is supplied as an aqueous dispersion containing 30 weight % solids. EUDRAGIT® L-30-D 55 aqueous copolymer dispersion is supplied by Rohm-Pharma Co., Germany.

In preparing enteric coated beads to form capsules of epothilone D, it may be desirable to include one or more subcoat layers that are situated between the epothilone D core and the enteric coating to minimize contact between those layers. For example, suitable materials to form the subcoat layer include starch; gelatin; sugars such as sucrose, glucose, dextrose, molasses, and lactose; natural and synthetic gums such as acacia, sodium alginate, methyl cellulose, carboxymethylcellulose, and polyvinylpyrrolidone (PVP) polymers and copolymers such as PVP-PVA copolymers; celluloses such as ethylcellulose, hydroxypropyl cellulose, and hydroxypropyl methyl cellulose; polyethylene glycol; and waxes. The subcoat layer may further comprise one or more plasticizers, such as polyethylene glycol, propylene glycol, triethyl citrate, triacitin, diethyl phthalate, tributyl sebecate, or combinations thereof.

The tablet or capsule of epothilone D optionally may comprise other materials such as flavoring agents, preservatives, or coloring agents as may be necessary or desired.

An appropriate dosage of epothilone D can be determined by one of skill in the art, taking into consideration the findings described herein together with typical factors such as the body mass of the patient, the physical condition of the patient, and so on. The dosage should contain epothilone D in an amount that is effective for treating Tau-associated diseases, including tauopathies such as AD. Generally, a range for the dosage of epothilone D administered for the treatment of Tau-associated diseases (including tauopathies such as AD) is considered to be between 0.0001-10 mg/m$^2$, more preferably between 0.001-5 mg/m$^2$. Other, more preferred dosage ranges for PO and IV administration are set forth above in the alternative embodiments section. The units mg/m$^2$, are used herein, for purposes of comparison with the chemotherapeutic dosages previously administered with epothilones and their analogs. However, the units mg/m$^2$ can be readily converted to mpk, considering the animal species receiving (or having received) the drug and the patient's bodyweight and/or height. For example, for a human patient weighing about 70 kg, the dose range of 0.0001-10 mg/m$^2$ converts to about 0.00003-0.3 mpk. Further information concerning dose conversions can be found at www.rphworld.com/viewlink-25045.html, and in Freireich et al., *Cancer Chemother. Reports*, 50(4):219 (1966).

The drug can be administered daily, weekly, or on an intermittent basis. For example, the drug can be administered for three weeks on, followed by one week off, or for two weeks on, followed by one week off, or under other dosing schedules as can be determined by one skilled in the field. The particular dose selected will depend upon the mode of administration and dosing regime selected. One preferred schedule is a once daily oral dosing schedule. When longer periods of time are prescribed between each application (typically the case for IV administration), each unit dose may be larger than when daily dosages are provided.

Notably, the dose of epothilone D that was administered to patients for treatment of cancer in certain Phase II clinical trials was 100 mg/m$^2$ administered as a 90 minute infusion given weekly for 3 of 4 weeks (i.e., on days 1, 8, and 15, every 4 weeks), following Phase I trials involving dose escalations of from 9 to 150 mg/m$^2$ for each dose. The dose of drug contemplated for treatment of AD is about ten-fold less, and more likely, about 100-fold less, and in another contemplated embodiment, even more than 1000-fold less, than the therapeutic dose of epothilone D that was administered for treatment of cancer patients in clinical Phase II trials, although the dosing schedule and mode of administration will influence the dose.

The present invention will be explained in further detail by way of non-limiting examples below, which make reference to the appended drawings. The following methods were used in the experiments described in the examples that follow the description of the methods.

Methods for Experimentals

Examples 1 Through 5

The creation of Tg4510, an aggressive Tau transgenic mouse line, was recently described (Santacruz et al., 2005; Berger et al., 2007). The Tg4510 line expressed Tau-P301L, a Tau mutant found in FTDP-17, using the calmodulin kinase II promoter. The Tg4510 line was unique in several respects:
1. High level of Tau expression (13-fold relative to mouse Tau);
2. Restriction of Tau expression to the frontal-temporal lobes (thereby avoiding the motoric deficits that had characterized previous Tau lines that expressed Tau in the spinal cord); and
3. Rapid and extensive neurodegeneration (60% CA1 neurons were lost by 5.5 months) preceded by cognitive deficits measurable at 4.5 months.

Drug Preparation for Tg4510 Study

Epothilone D (Compound I) was dosed intraperitoneally with a 26-gauge needle, in 10% ethanol, 90% water, 10 ml/kg at 0 (vehicle), 1 mpk, and 10 mpk. A 10× stock solution was made in 100% ethanol, and diluted just before dosing. Mice were dosed in 3 cohorts and data were combined to give a final N of 12, 9, and 15 for the vehicle, 1 mpk, and 10 mpk groups, respectively. Mice were dosed in a chemical fume hood.

Injection and Behavioral Testing Schedule for Tg4510 Study

Tg4510 mice were used in this study. These mice are a well-characterized, aggressive model of tauopathy that over-express human P301L mutant Tau in the forebrain (Santacruz et al., 2005; Berger et al., 2007). The mice are characterized by accumulations of abnormal forms of Tau, including tangles similar to those observed in AD brain, behavioral deficits, and eventually neuronal loss. At 9 weeks (+/-15 days) of age, mice were acclimated to handling with a single mock injection of phosphate buffered saline, performed within a chemical fume hood. The mice were then housed in cages kept within the chemical fume hood for 48 hours. Following the 48-hour period, the mice were transferred to clean cages and brought to a behavioral suite for testing.

The mice were then tested in a Morris water maze (MWM) for six days. The mice were distributed into treatment groups based on the results of the behavioral analysis using the rank scores for probe trial 2 annulus crossing index. Mice were 11 weeks (+/-15 days) of age at the start of dosing and were dosed once weekly. A panel of neurological and physical propensity tests (Modified SHIRPA) were performed following the first week of dosing, including analysis of body position, tremor, coat appearance, gait, touch escape, positional passivity, limb grasping, and righting reflex. Mice were additionally examined 48 hours after each weekly dose for coat appearance, limb grasping, righting reflex and for any overt stereotyped behavior. No signs of overt toxicity, weight loss, or motor deficits were observed in the course of the study.

Mice were again tested in the MWM after the eighth dose (19 weeks of age+/-15 days) for six days. After behavioral testing, dosing resumed until the animals were 5.5 months of age at the time of harvest. Animals were housed and treated according to Institutional Care and Animal Use Committee and National Institutes of Health standards.

Morris Water Maze Protocol

Mice were tested in Morris water maze (MWM) on two occasions, once prior to dosing, and once two months after dosing began. The second round of water maze testing was performed in another testing room. Mice were acclimated to the experimental room for 2-3 days prior to testing. The mice were placed in a water maze of 1.5 m diameter, with a 16 cm diameter platform placed 0.5-1.0 cm under the surface of the water. The water was made opaque with non-toxic white paint and the water temperature was regulated between 22-25° C.

The mice were given 4 trials per day of up to 90 seconds each with a 10 second rest period on the platform after each trial. If the mouse did not find the platform within 90 seconds, the mouse was gently guided to the platform and allowed to remain there for 10 seconds. The testing room rooms each had large external cues to allow the mice to orient as they learned the location of the platform. Mice were placed under a heat lamp to prevent hypothermia after each trial. The interval between trials ranged from 25 to 45 minutes. The mice were tracked using HVS Image Advanced Tracker VP200 software (Buckingham, UK) and the total distance traveled until reaching of the platform was determined.

Statistical analysis for acquisition path length from the five trials involved a repeated measures analysis of variance. The statistical model included "treatment" (0, 1 mpk, or 10 mpk of epothilone D (Compound I)) as a between animal term, and the 5 trials as repeated measures on each animal. If the analysis indicated a significant effect of treatment, or a treatment-by-trial interaction, differences between the 1 mpk and 10 mpk groups were compared to the vehicle group using Dunnett's test. The probe pathlengths in each quadrant, and number of platform crossings in each quadrant, were analyzed using Dunnett's test. In all cases, 1 mpk and 10 mpk groups were compared to the vehicle group. All calculations were done in SAS, version 9.1, under the Windows XP Professional operating system.

Acquisition training was performed for 5 consecutive days. A Probe trial was performed 18 h after the last acquisition training on day 6. During these 60 second trials, the platform was removed, and the distance that the mouse spent in the target quadrant and the number of crossings of a region where the platform was previously located were measured. Swim speed was monitored for all animals; drug treatment did not cause any changes in swim speed consistent with the drug not affecting motor behavior. Float time (swim speeds of <5 cm/sec) also did not vary between treatment groups.

Tissue Harvesting

Mice were euthanized by cervical dislocation at 5.5 months followed by decapitation. Brains were immediately removed and divided down the midline into two hemispheres. The right hemisphere was placed into 20 mL of 4% paraformaldehyde (prepared fresh on the day of sacrifice) and stored overnight at 4° C. The following day, the brains were transferred to a tube containing 20 mL TBS (pH 7.4, 20 mM TRIS, 100 mM NaCl) and then stored at 4° C. until processing. Right hemispheres were embedded in paraffin, sectioned at 5 microns, and mounted on positively charged glass slides. The slides were dried overnight in a 60° C. oven and stored at room temperature until stained. The left hemispheres were frozen (within 2 minutes) on dry ice.

Gallyas Method

The Gallyas staining method was used to detect silver-positive neurofibrillary tangles and dystrophic neurites. Paraffin-embedded thin sections (5 microns) mounted on glass slides were deparaffinized and rehydrated via serial incubation in xylene (two times for 10 minutes each), 100% ethanol (two times for 10 minutes each), 95% MeOH/5% $H_2O_2$ (30 minutes), 95% ethanol (two times for 5 minutes each), 80% ethanol (two times for 5 minutes each), 50% ethanol (two times for 5 minutes each), and water (two times for 5 minutes each). The sections were then placed into 5% periodic acid for 5 minutes, washed in $dH_2O$ two times for 5 minutes each time, and placed in alkaline silver iodide solution (containing 1% silver nitrate) for 1 minute.

The sections were washed in 0.5% acetic acid for 10 minutes, placed in freshly prepared developer solution for 15 minutes, and washed again in 0.5% acetic acid for 5 minutes. Following a rinse in deionized water, the sections were placed in 0.1% gold chloride for 5 minutes and rinsed again in deionized water. The sections were incubated in 1% sodium thiosulphate (hypo) for 5 minutes and then rinsed in tap water. Counterstain was performed in 0.1% nuclear fast red for 2 minutes. The sections were then rinsed in tap water, dehydrated in graded series of alcohol (95%, 100%, 100%) for 2 minutes, and cleared in 3 changes of xylene, 10 dips each. Finally, Cytoseal 60 mounting medium and cover slips were added to the slides (Richard-Allan Scientific of Kalamazoo, Mich.). Statistics was performed using the non-parametric Kruskal-Wallis test, followed by Dunn's multiple comparison test using Graphpad Prism 4. The same results were obtained with the parametric ANOVA followed by Dunnett's post-hoc test.

Immunohistochemistry

Paraffin-embedded thin sections (5 microns) were deparaffinized and rehydrated to water in 3 changes of xylene, two changes of 100% ethanol, and 1 change of 95% ethanol, followed by rinsing in water. Antigen retrieval was performed by steaming the slides in 10 mM sodium citrate buffer, pH 6.0 for 30 minutes in a Black and Decker Steamer (Model # HS900) and then cooled for 30 minutes. Endogenous peroxidase activity is removed by incubation in 0.6% hydrogen peroxide in 90% MeOH for 15 minutes. After washing in TBS, slides are blocked in 10% normal goat serum in TBS for one hour. This is followed by incubation of the AT8 phospho-Tau antibody (Pierce Biotechnology Inc., Rockford, Ill., Goedert et al., 1995) diluted in the blocking solution overnight at 4° C. After 3 washes in TBS, the slides are incubated with an anti-mouse IgG antibody for 1 hour at room temperature. After washing in TBS, the signal is detected using a Vectastain ABC Elite Kit (Vector Labs Burlingame, Calif.) for 1 hour followed by detection using the diaminobenzadine reagent from Vector labs. Nuclei were counterstained blue with hematoxylin, followed by dipping slides 2 times in Scott's tap water substitute (Surgipath #02900, Richmond, Ill.) and then rinsing in tap water. The sections were then dehydrated in graded series of alcohol (95%, 100%, 100%) then cleared in 3 changes of xylene. Cover slips and Cytoseal 60 mounting medium were then added.

Stereology

Nissl stained slides were scanned and digitized using the Aperio ScanScope (Aperio Technologies, Inc., Vista, Calif.). Images of the entire brain section were captured at high resolution and stored as files within Spectrum (Aperio software). To process images, a region of 4,000×4,000 pixels including the entire hippocampus was captured using the extract tool and saved as a JPEG file for importing into Metamorph (Molecular Devices, Sunnyvale, Calif.) for quantification of cell loss within the CA1 and CA3 regions of the hippocampus. A modified version of the single section dissector method (Moller et al. 1990) was utilized to quantify cell loss because of its suitability for thin, paraffin-embedded tissue sections. To obtain relative numbers of cells, every fifth section was collected as the paraffin-embedded brains were cut sagitally between the Bregma and approximately 0.75 mm laterally. Three regions were drawn and counted per section using Metamorph software. The same regions were used for every image and 5 sections were counted per animal, 5 slides apart. Statistics were performed using ANOVA followed by Dunnett's post-hoc test.

Example 1

Figure 1:
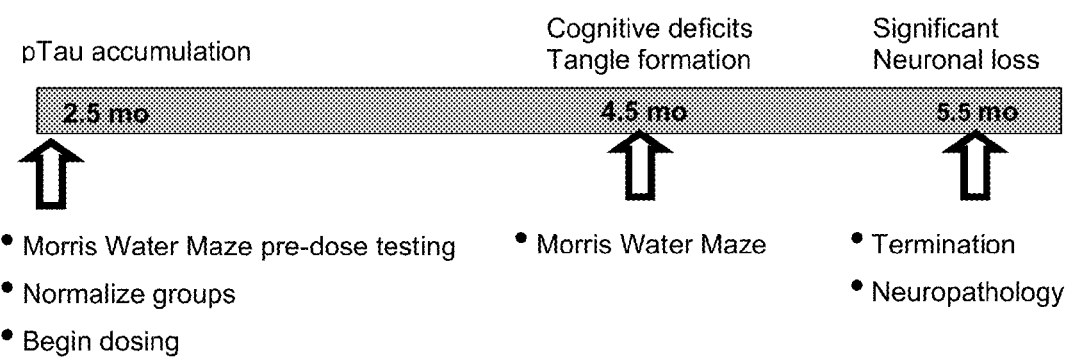
FIG. 1 shows the basic design of an experiment on Tg4510 mice using epothilone D (Compound I).

The design of the Tg4510 experiment with epothilone D (Compound I) as described above is depicted in FIG. 1. In this experiment, mice were tested at 2.5 months in the MWM and assigned to one of three groups (N=12, 13, 16) such that the pre-treatment performance of each group was determined to be similar. Starting at 2.5 months, mice were administered a weekly intraperitoneal (IP) injection of either vehicle alone or vehicle with 1 mpk or 10 mpk of epothilone D (Compound I). At 4.5 months, the mice were again tested in the MWM to determine the effect of treatment on cognitive performance. After 5.5 months, mice were euthanized and brains were collected for subsequent analysis.

In tumor xenograft experiments, investigators typically administer epothilone D (Compound I) intraperitoneally at 30 mpk every other day for 5 days, yielding a cumulative dose of 150 mpk. (Chou et al., 1998) Hence, treatment with 1 mpk epothilone D (Compound I) for 12 weeks, as described herein, is considered to be about 100-fold below the oncology dose, with the treatment at 10 mpk being about 10-fold below the typical oncology dose administered in this type of experiment. When mice were dosed once weekly intraperitoneally with 1 mpk and 10 mpk epothilone D (Compound I) for 2 or 6 months, no histopathological abnormalities were observed in multiple tissues, including liver, kidney, heart, testes, adrenal gland, bone marrow, peripheral nerve, stomach, and small and large intestines.

Figure 2:
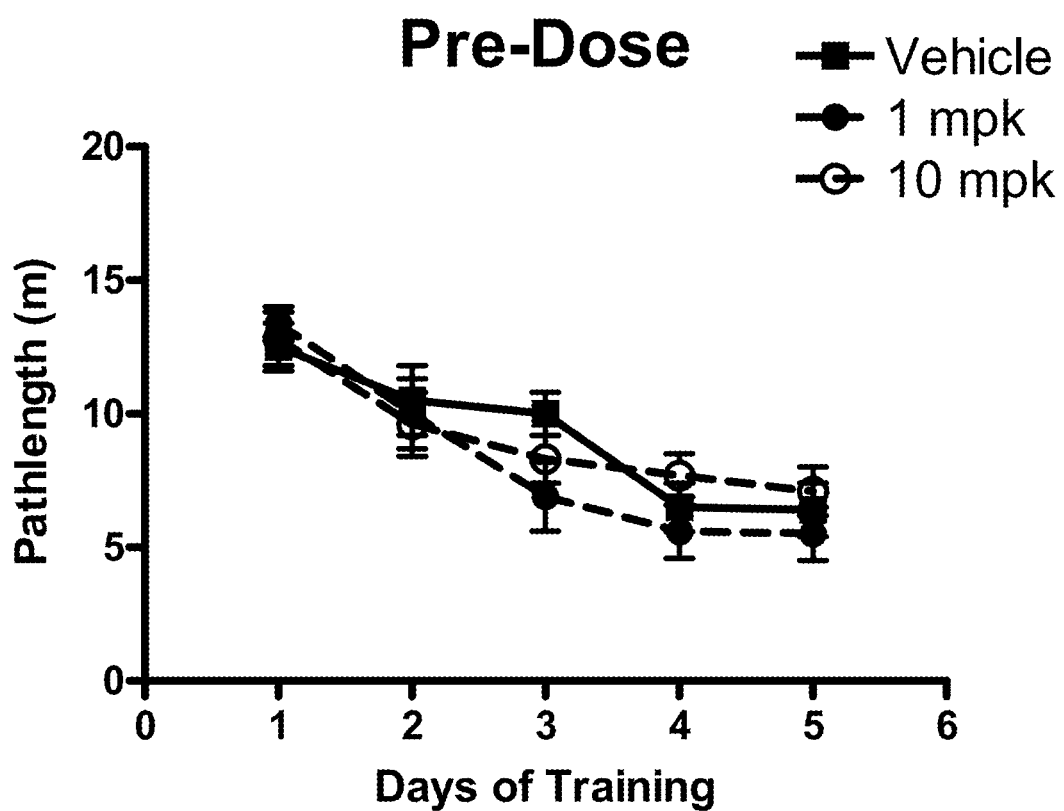
FIG. 2 shows the results of a Morris water maze (MWM) test of the Tg4510 mice at 2.5 months, prior to dosing with epothilone D (Compound I).

FIG. 2 shows the results of a MWM test of the Tg4510 mice at 2.5 months, prior to dosing with epothilone D (Compound I) or with vehicle. There were no statistically significant differences between the groups prior to dosing in acquisition or during probe trials, which was the basis for separating animals into groups. In other words, FIG. 2 operates as a control in showing the pre-treatment performance of each group was similar.

Figure 3:
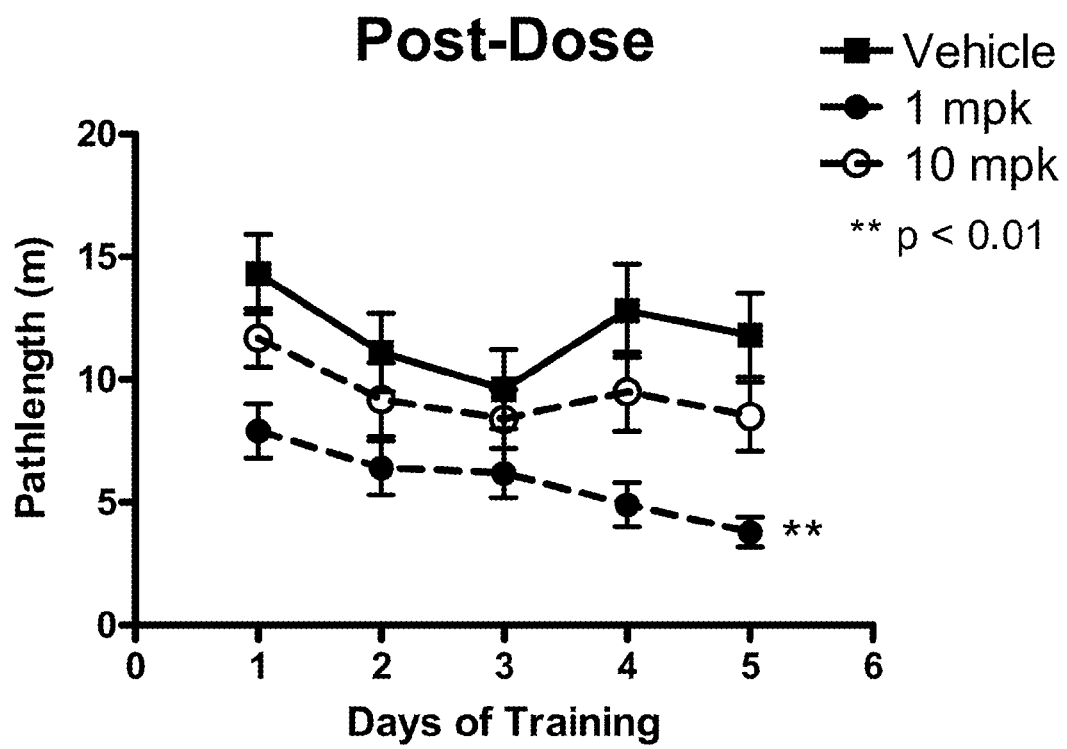
FIG. 3 shows the results of a MWM test of the Tg4510 mice at 4.5 months, after 2 months of dosing with epothilone D (Compound I).

The Tg4510 mice were then administered epothilone D (Compound I)) once weekly intraperitoneally at 1 mpk, 10 mpk, and with vehicle, and the MWM test was performed at 4.5 months, following this weekly dosing over 12 weeks. The results which are reported in FIG. 3, revealed that mice treated with 1 mpk epothilone D (Compound I) were able to locate the hidden platform in the MWM more quickly (i.e., in a statistically significant manner ($p<0.01$)), than could mice that were treated with the vehicle. The 10 mpk treatment group showed a trend toward improvement as compared with the vehicle group. These findings show that treatment of Tg4510 mice with epothilone D (Compound I) led to statistically significant improved cognitive function relative to vehicle treatment, and additionally, that the lower dose of 1 mpk generated improved results as compared with the higher dose (10 mpk). Notably, the inventors herein further confirmed that the exposure using this paradigm was dose dependent based on separate experiments comparing 1 mpk and 10 mpk doses in mice. For this reason, the reduced behavioral improvement in the 10 mpk group, relative to the 1 mpk group, was not due to unanticipated, reduced drug levels in the 10 mpk treated animals.

Example 2

Figure 4:
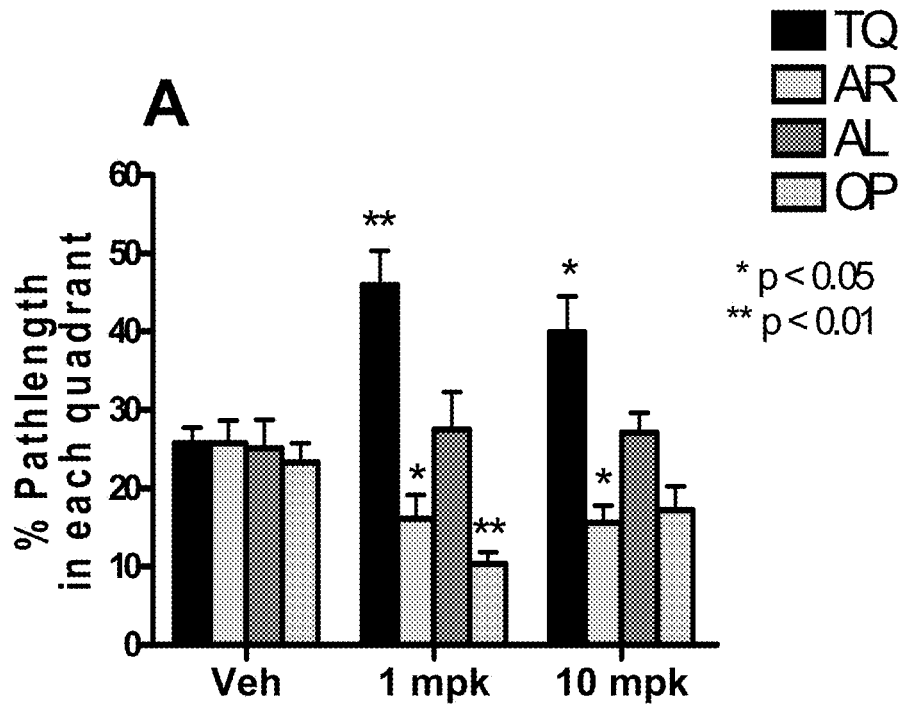
FIG. 4 shows probe data 18 hours after 5 days of training in the 4.5 month-old Tg4510 mice dosed for 2 months with epothilone D (Compound I). "TQ" stands for target quadrant, "AR" stands for adjacent right, "AL" stands for adjacent left, and "OP" stands for opposite quadrant. Two measures of performance, namely % pathlength (A) and number of platform crossings (B) are described.
Figure 4:
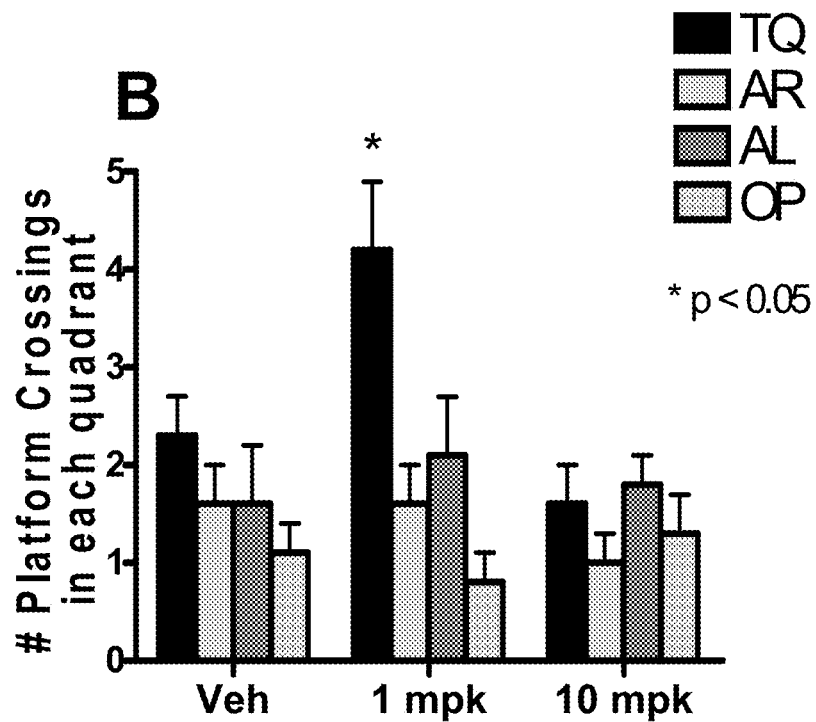

FIG. 4 shows probe data 18 h after 5 days of training in the 4.5 month-old Tg4510 mice dosed for 2 months with epothilone D (Compound I) at 1 mpk, 10 mpk, and with vehicle. In FIG. 4, "TQ" stands for target quadrant, "AR" stands for adjacent right, "AL" stands for adjacent left, and "OP" stands for opposite quadrant. Two measures of performance, namely % pathlength (A) and number of platform crossings (B) in each quadrant, are indicated in FIG. 4. A preference for the target quadrant indicates that the mouse remembered the location where the platform was located during the acquisition phase of the study. As can be seen from the data, the vehicle-treated mice performed at chance with similar results for each of TQ, AR, AL, and OP, for both the pathlength (A) and platform crossing (B) measures, and they did not show a quadrant preference. However, the mice treated with 1 mpk (Compound I) showed statistically significant differences in both measures as compared with the vehicle group in memory, e.g., in recalling that the platform had been located at the TQ. Additionally, the 10 mpk group showed significantly greater performance compared to the vehicle group in the % pathlength measure (A) but not when using the number of platform crossings measure (B).

Example 3

Figure 5:
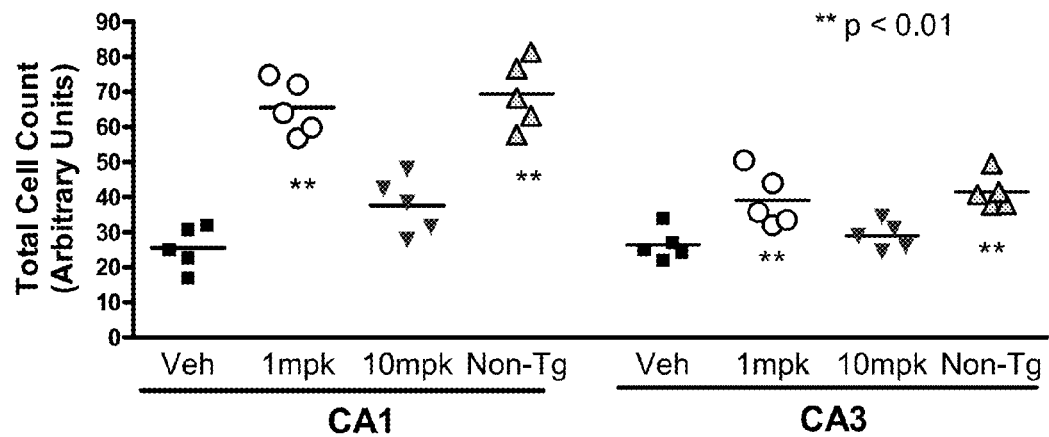
FIG. 5 shows neuronal counts in the CA1 and CA3 regions of the hippocampus in Tg4510 mice at 5.5 months following treatment with vehicle, 1 mpk epothilone D (Compound I), and 10 mpk epothilone D (Compound I).

To determine the effect of epothilone D (Compound I) on brain pathology, brain tissue was examined from a subset (N=5) of the Tg4510 mice from the preceding experiment. Previous studies had shown that Tg4510 mice lost about 60% of their neurons in the CA1 region of the hippocampus at 5.5 months (Santacruz et al. 2005). Thus, the present inventors first examined the number of the neurons in the CA1 region of the hippocampus, followed by examination of the CA3 region. FIG. 5 depicts neuronal counts in the CA1 and CA3 regions of hippocampus in the mice at 5.5 months following treatment with vehicle, 1 mpk of epothilone D (Compound I), and 10 mpk of epothilone D (Compound I).

Surprisingly, as can be seen in FIG. 5, the Tg4510 mice treated with 1 mpk epothilone D (Compound I) had substantially more CA1 neurons than vehicle-treated animals. In fact, the difference between the mice treated with vehicle and the mice treated with 1 mpk of epothilone D (Compound I) shows that the 1 mpk of epothilone D (Compound I) prevented neuronal loss with a statistically significant difference from vehicle ($p<0.01$). The mice treated with 10 mpk of epothilone D (Compound I) had CA1 neuronal levels that were intermediate between the vehicle-treated mice and the mice treated with 1 mpk of epothilone D (Compound I). These results are consistent with and reinforce the findings from the behavioral studies of Examples 1 and 2, i.e., showing that the 100-fold lower dose (i.e., than the chemotherapeutic dosages administered in tumor xenograft experiments) consistently produced significantly improved results in treating tauopathy.

A similar trend was also observed for the total cell counts of CA3 regions of the hippocampus, with significant differences between the 1 mpk and non-transgenic mice compared to vehicle treated mice. The elevation in cell count at the CA3 region in the treated group was less pronounced than in the CA1 region where there is more neurodegeneration at this age; however, these results show an impact on underlying disease in multiple regions of the brain.

Example 4

The effect of treatment on phosphorylated Tau staining in the CA1 region was also examined. The AT8 antibody recognizes Tau that is phosphorylated on both the 202 and 205 residues. This form of hyperphosphorylated Tau is greatly enriched in AD and other Tauopathy patient brains. (Goedert et al. 1995).

Figure 6:
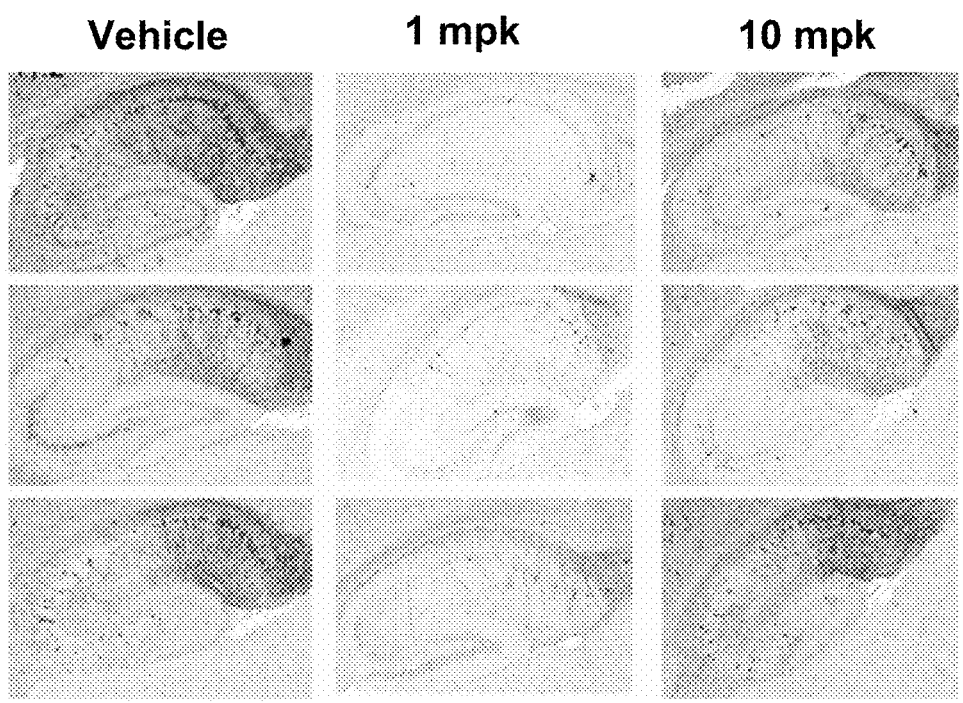
FIG. 6 shows phosphorylated Tau staining of the Tg4510 mice treated with vehicle, 1 mpk epothilone D (Compound I), and 10 mpk epothilone D (Compound I) in the hippocampus.

FIG. 6 shows AT8 phosphoTau staining of the Tg4510 mice treated with vehicle, 1 mpk epothilone D (Compound I), and 10 mpk epothilone D (Compound I) as described above. PhosphoTau staining is indicated in dark black. Surprisingly, the mice treated with 1 mpk of epothilone D (Compound I), showed much less phosphoTau staining, particularly in comparison to the vehicle-treated mice. Mice treated with 10 mpk of epothilone D (Compound I) showed intermediate levels of phosphoTau staining.

Example 5

The effect of treatment with epothilone D (Compound I) on neurofibrillary tangle formation in the cortex was examined by Gallyas silver staining FIG. 7A shows Gallyas silver staining for neurofibrillary tangles in the frontal cortex of the Tg4510 mice treated with vehicle, 1 mpk of epothilone D (Compound I), and 10 mpk of epothilone D (Compound I) as described above. In FIG. 7A, silver staining is in black (positive), and "NT" stands for non-transgenic, demonstrating some non-specific staining associated with blood vessels. As can be seen in FIG. 7A, the mice treated with 1 mpk of epothilone D (Compound I) had much lower levels of neurofibrillary tangles than did vehicle-treated mice; this is quantitated for all animals in the study in FIG. 7B. A significant impact on underlying disease in both cortex and hippocampus was observed at the 1 mpk dose, with the 10 mpk dose again showing a trend toward improvement.

As described in the preceding Examples, treatment of Tg4510 mice with epothilone D (Compound I) prevented cognitive decline and improved cognitive function over time as compared with the untreated Tg4510 mice. Furthermore, neuropathological tests as measures of impact on underlying disease (i.e., cell count, phosphoTau staining, and silver staining tests), demonstrate that treatment with epothilone D prevents neuronal loss, reduces accumulation of abnormal Tau, and prevents the formation of neurofibrillary tangles at statistically significant levels as compared with untreated Tg4510 mice. Thus, the inventors herein believe they are the first to discover and demonstrate the prevention of cognitive loss, Tau pathology, and neurodegeneration upon treatment with a microtubule-stabilizing compound, namely, epothilone D.

Additionally, the inventors herein have discovered that the therapeutic effects achievable upon treatment with epothilone D is likely non-linearly dose dependent. Specifically, consistent dose-dependent results were repeatedly obtained in each of the behavioral and neuropathological studies reported, wherein at the lower dose (1 mpk) (about 100-fold less than the chemotherapeutic dose in tumor xenograft experiments), a significantly-enhanced beneficial effect was obtained in all measures as compared with the vehicle, while the higher dose (10 mpk), showed a trend toward effect with most measures and a statistically significant difference over vehicle in one measure of the MWM probe test.

Example 6

Epothilone D Performance Compared with Other Microtubule-Stabilizers in Bolus IV Experiments In one group of experiments, ixabepilone (aza-epothilone B analog), Compound II (BMS 310705, 21-amino epothilone F), and epothilone D (Compound I) were evaluated and compared to paclitaxel after bolus IV administration into the tail veins of nude mice at dosages of 1 to 12 mpk with 3 mice/group. Each of the four compounds were dosed at 5 ml/kg using 10% Cremophor, 10% ethanol, and 80% water containing 5% dextrose. To determine the relative brain penetrance of each compound, the plasma, brain, and liver levels of the compounds were measured at various times after a single dose using liquid chromatography with tandem mass spectrometry (LC/MS/MS) after an organic phase extraction, as reported in FIGS. 8A-8D and Table 1. Liver levels were not measured in the paclitaxel treated mice.

Figure 8A:
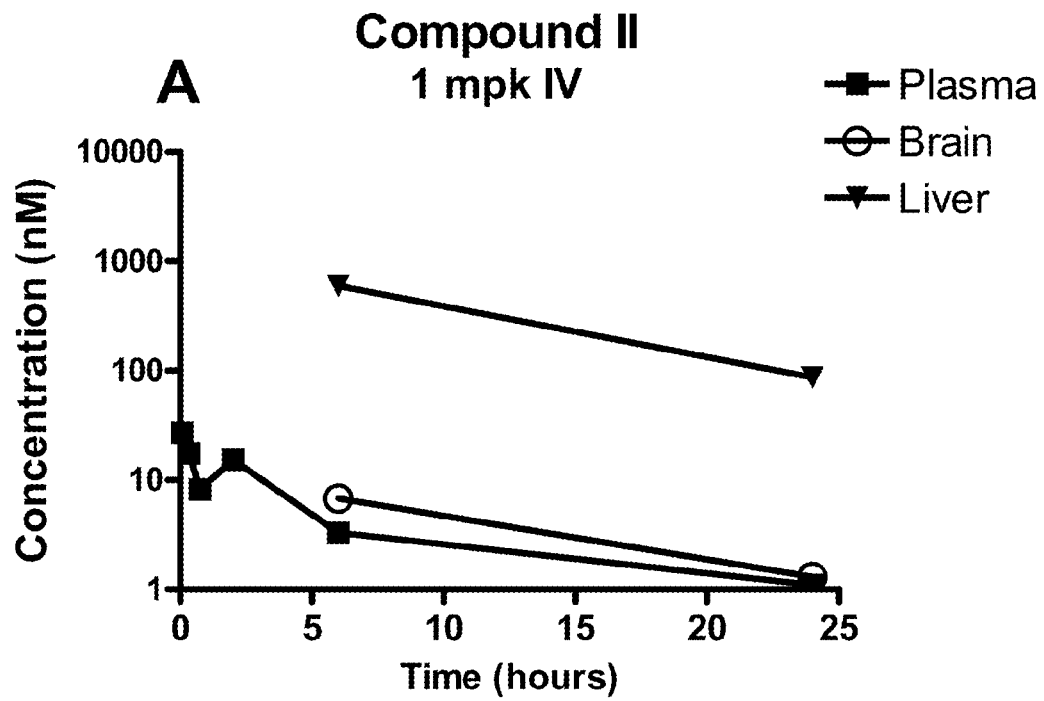

FIG. 8A shows the concentration of Compound II in the plasma, brain, and liver of mice following IV administration at 1 mpk at various times.

Figure 8B:
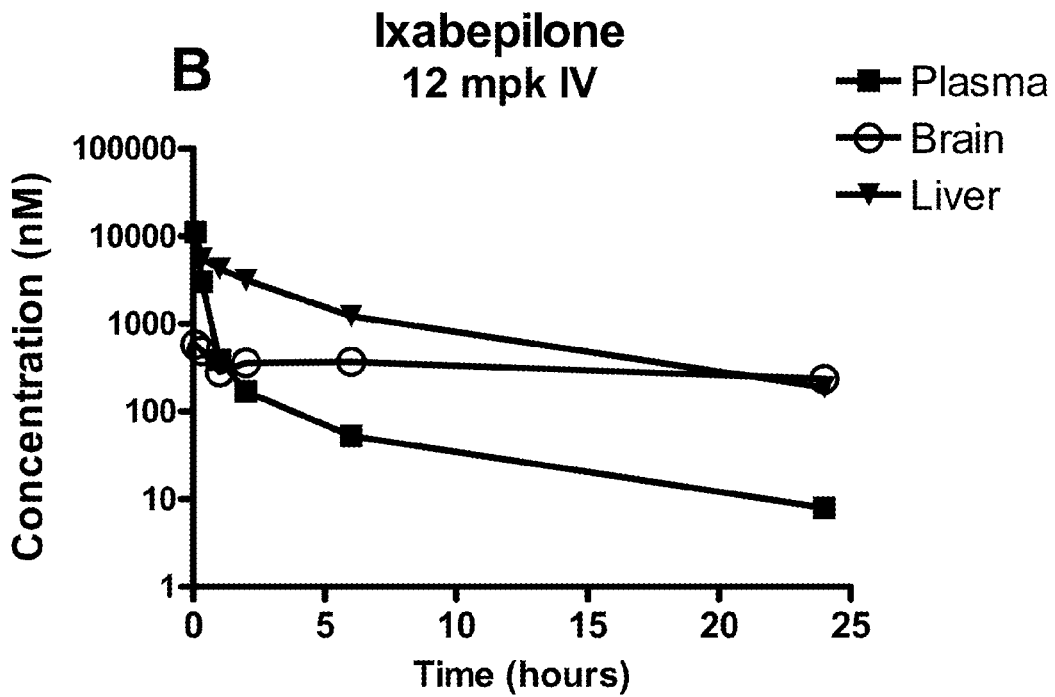

FIG. 8B shows the concentration of ixabepilone in the plasma, brain, and liver of mice following IV administration at 12 mpk at various times.

Figure 8C:
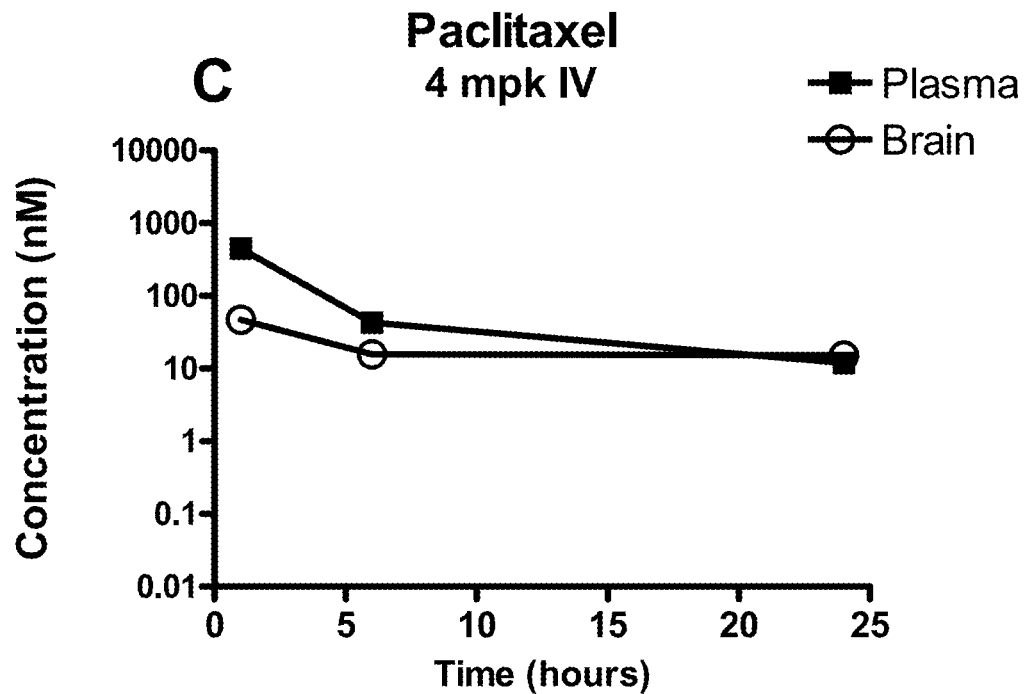

FIG. 8C shows the concentration of paclitaxel in the plasma and brain of mice following IV administration at 4 mpk at various times.

Figure 8D:
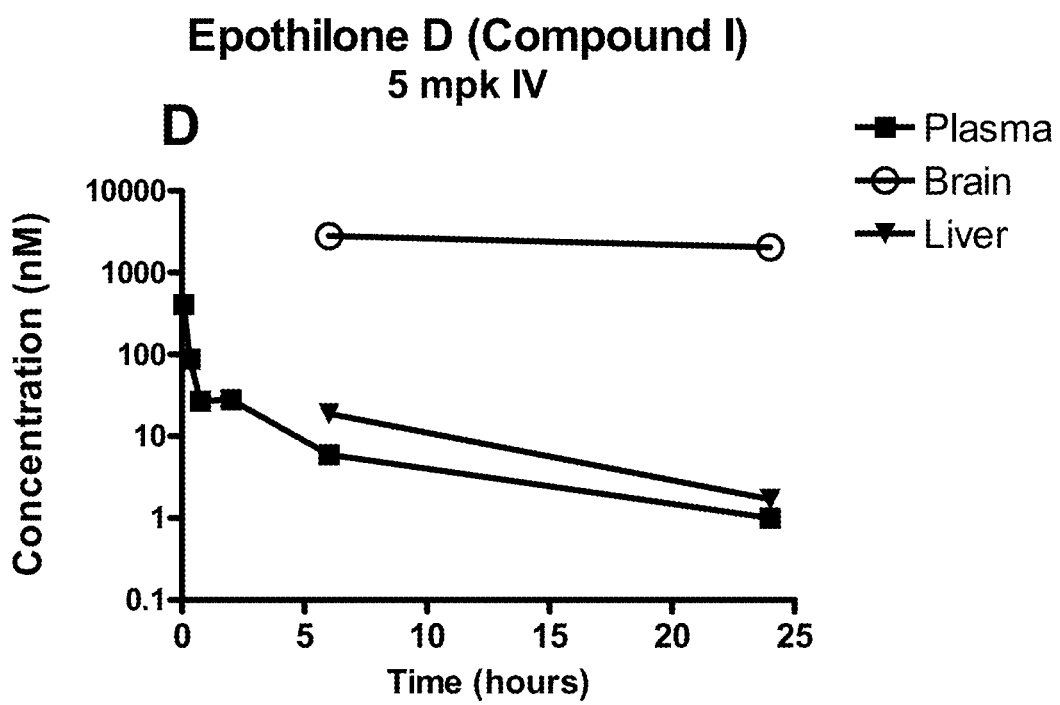

FIG. 8D shows the concentration of epothilone D (Compound I) in the plasma, brain, and liver of mice following IV administration at 5 mpk at various times.

The data showed that Compound II and ixabepilone had modest brain levels relative to peripheral tissue as measured by the ratio of the brain-to-liver compound levels, particularly at later times after the initial distribution and clearance of plasma drug. As expected, paclitaxel brain levels were low. In particular, paclitaxel brain levels did not exceed plasma drug levels for at least 24 h after dosing. Unexpectedly, epothilone D (Compound I) had the combined properties of remarkably better brain penetration and selective retention than the compounds tested in this experiment, as evidenced by high brain levels that exceeded liver levels at 6 and 24 h after dosing. This demonstrates unexpected retention of epothilone D (Compound I) in the target organ (brain) relative to the periphery, including the plasma and tissues, most notably the liver, which is a potential site of toxicity.

More specifically, Table 1 reports comparative brain penetration data for four microtubule stabilizers—paclitaxel, Compound II (BMS 310705), ixabepilone, and epothilone D—after bolus IV dosing (varied mpk, as reported in the table) using nude mice, which data is also reflected in FIGS. 8A-8D. The brain-to-plasma ratio generally increases with time after dosing for each compound due to the rapid loss from the plasma and retention of the drug in the brain by binding to microtubules. The brain-to-plasma ratio may then fall for compounds where there is less retention in the brain, such as is observed for Compound II showing a decrease between 6 and 24 h. Despite the change in brain-to-plasma ratio with time, this ratio provides a measure of the intrinsic brain penetration for a compound when data from short times after dosing (e.g., between 20-60 minutes following dosing) are compared. In the Tables herein, brain-to-plasma and brain-to-liver ratios were calculated by first calculating the ratios for individual animals, and then determining the mean of the ratios; the Tables herein report the mean values thus obtained.

TABLE 1

| Compound | Dose (mpk) | Time (hr) | Plasma conc (nM) | Brain conc (nM) | Brain-to-plasma Ratio | Brain-to-Liver Ratio |
|---|---|---|---|---|---|---|
| Paclitaxel | 4 | 1 | 447 | 47 | 0.10 | NQ |
|  |  | 6 |  | 43 | 16 | 0.37 | NQ |
|  |  | 24 | 12 | 15 | 1.25 | NQ |
| Compound II | 1 | 6 | 3 | 6.8 | 2.1 | 0.01 |
|  |  | 24 | 1 | 1.3 | 1.2 | 0.02 |
| Ixabepilone | 12 | 0.12 | 11,236 | 579 | 0.05 | 0.05 |
|  |  | 0.33 | 3057 | 495 | 0.16 | 0.09 |
|  |  | 1 | 390 | 284 | 0.73 | 0.07 |
|  |  | 2 | 171 | 360 | 2.1 | 0.11 |
|  |  | 6 | 53 | 371 | 7.0 | 0.30 |
|  |  | 24 | 8 | 236 | 30 | 1.2 |
| Epothilone D | 5 | 6 | 6 | 2794 | 470 | 149 |
|  |  | 24 | 1 | 2046 | 2046 | 1204 |

Looking at Table 1, paclitaxel is poorly brain penetrant as evidenced by a brain-to-plasma ratio of 0.1 at 1 hour after dosing; ixabepilone is more brain penetrant than paclitaxel with a brain-to-plasma ratio of 0.73 at 1 hour after dosing (Table 1). At times from 6-24 h after dosing, the brain-to-plasma ratio is a reflection of both intrinsic brain penetration and retention (half-life) in the brain. The data at 6 and 24 h after dosing of epothilone D shows at least a 60-fold increase in brain-to-plasma ratio above ixabepilone, the compound with the next highest brain-to-plasma ratio in this group.

The brain-to-liver ratios not only provide a more singular measure of brain retention and half life, but also selective retention compared to peripheral tissues. This is valuable because the liver, chosen largely because it is well perfused and tends to have higher levels than many other peripheral tissues, contains microtubules where the compound can be retained, unlike the non-cellular plasma. In contrast to the brain-to-plasma ratio where the optimal measurement time is in the 20-60 minute range, it is preferable to compare the brain-to-liver ratios at later times after dosing (e.g., 24 h or more), when the plasma levels have significantly decreased, thereby allowing a more accurate measure of the drug that is specifically retained within brain and liver cells. A comparison of the brain-to-liver ratios shows that epothilone D is highly, selectively retained in the brain relative to the liver. For instance, the 24 hour brain-to-liver ratio of epothilone D is 1204, a remarkably, much higher ratio as compared with the lower ratios for ixabepilone (1.2) and Compound II (0.02) in the same set of experiments.

In a separate experiment, epothilone D plasma and brain concentrations were evaluated for longer periods of time, i.e., up to 168 h, following bolus IV administration, using a similar protocol as described above, but with middle-aged triple transgenic mice (Oddo et al. 2003), in the hands of different scientists. The results of this experiment are reported below in Table 2 and in FIG. 10.

TABLE 2

(EPOTHLONE D ONLY)

| Time (hr) | Plasma conc (nM) | Brain conc (nM) | Brain/Plasma Ratio | Brain/Liver Ratio |
|---|---|---|---|---|
| 0.05 | 25,100 | 1127 | 0.04 | 0.42 |
| 0.17 | 2003 | 595 | 0.28 | 1.1 |
| .33 | 549 | 529 | 0.86 | 0.38 |
| 1 | 325 | 422 | 1.2 | 0.42 |
| 3 | 70 | 468 | 6.1 | 0.30 |
| 6 | 43 | 141 | 3.3 | 0.24 |
| 16 | 0.8 | 210 | 265 | NQ |
| 24 | 0.9 | 82.7 | 89 | NQ |
| 96 | <LLQ (0.6 nM) | 25.2 | NQ | NQ |
| 168 | <LLQ (0.6 nM) | 16.3 | NQ | NQ |

These data demonstrate the extended retention of epothilone D in brain tissue to at least 168 h (7 days) after a single dose. The absolute brain levels and ratios in Tables 1 and 2 for epothilone D vary; it is important to note that the experiments described in Tables 1 and 2 were separately performed at different times by different scientists with different strains of mice. The inventors have observed that small differences in IV injection time can alter the exact exposure profile, particularly the maximal plasma concentration, which will influence the brain concentration, and further, that the IV injection time can differ between scientists. For this reason, it is best to compare the results within a single experiment. Despite this issue, the overall trends and relative characteristics of the microtubule-stabilizers as compared with each other are consistent, and these results show that epothilone D is highly brain penetrant with substantially improved brain penetration and retention as compared with Compound II, ixabepilone, and paclitaxel. For example, even when engaging in a comparison of data obtained from two separate experiments, the brain-to-plasma ratio of epothilone D at 6 h after dosing was 2046 in Table and 89 in Table 2, still markedly greater than the ratios at the same times for paclitaxel (0.37), and Compound II (2.1) in Table 1. Because the liver levels in the study described in Table 2 fell below the lower level of quantitation (LLQ of 49 nM in this study) at 24 hr, a brain-to-liver ratio was not quantifiable (NQ) at this time.

WO 03/074053 A1 broadly discloses the use of certain epothilones for the treatment of brain diseases. According to that publication, plasma and brain levels for three epothilones (not including epothilone D) were measured during the first 40 minutes following bolus IV administration at 5 mpk. The brain and plasma concentration data reported in WO 03/074053 A1 for what is identified therein as compound 1: 4,8-dihydroxy-16-(1-methyl-2-(2-methyl-4-thiazolyl)-ethenyl)-1-oxa-7-(1-propyl)-5,5,9,13-tetramethyl-cyclohexadec-13-ene-2,6-dione, and paclitaxel, are reproduced in Table 1 below. Data was reported in WO 03/074053 according to the units, µg/ml, and in minutes; this data was converted to nM and is reported in Table 3 in nM and hr, for purposes of comparison. This data (per Table 3) was not independently confirmed by the inventors herein but rather, it is reproduced based on the values presented in that publication (as converted to hr and nM). Additionally, it is noted stereoisomerism and/or a method of preparation are not reported for compound 1 within WO 03/074053, and a 13 E/Z mixture is referenced (see page 13, line 15).

TABLE 3

| Compound | Time (hr) | Plasma conc. (nM) | Brain conc. (nM) | Brain-to-plasma Ratio |
|---|---|---|---|---|
| Compound III | 0.17 | 1540 | 580 | 0.4 |
|  | 0.33 | 1150 | 1540 | 1.3 |
|  | 0.67 | 580 | 1150 | 2 |
| Paclitaxel | 0.17 | 940 | <LLQ | NQ |
|  | 0.33 | 700 | <LLQ | NQ |
|  | 0.67 | 230 | <LLQ | NQ |

Because the data was reported to only 40 minutes, only brain penetration can be assessed from this study by examining the brain-to-plasma ratio. Paclitaxel is presumed to have poor brain penetrance (consistent with the data in Table 1) because the brain levels are below LLQ, although the level of detection was not disclosed. Measures of brain retention which need to be measured at least 24 h post-dosing, and selective brain penetration by comparison with peripheral tissues were not discussed in WO 03/074053 A1.

Example 7

Epothilone D Performance Following Oral Administration

To further analyze epothilone D's performance in treating tauopathies, the compound was evaluated in two experiments involving administration to C57BL/6 mice at 10 mpk and 35 mpk by oral gavage, respectively. Additionally, in these experiments, an isomer of 4,8-dihydroxy-16-(1-methyl-2-(2-methyl-4-thiazolyl)-ethenyl)-1-oxa-7-(1-propyl)-5,5,9,13-tetramethyl-cyclohexadec-13-ene-2,6-dione (Compound III herein), was also evaluated and a side-by-side comparison made as between epothilone D and Compound III. Below, we first report the experimental detail for preparation and isolation of Compound III, and then the biological, in vivo data is described.

General Experimental Information

In the following procedures, all temperatures are given in degrees Celsius. $^1$H-NMR spectra were run on a Bruker 500, 400, or 300 MHz instrument and chemical shifts were reported in ppm ($\delta$) with reference to tetramethylsilane ($\delta$=0.0). All evaporations were carried out under reduced pressure. Unless otherwise stated, LC/MS analyses were carried out on a Waters instrument using a Phenomenex-Luna 3.0×50 mm S 10 reverse phase column employing a flow rate of 4 mL/min using a 0.1% TFA in MeOH/water gradient [0-100% in 3 min, with 4 min run time], and a UV detector set at 220 nm or Phenomenex-Luna 3.0×50 mm 10u reverse phase column employing a flow rate of 5 mL/min using a 10 mM ammonium acetate acetonitrile/water gradient [5-95% in 3 min, with 4 min run time] and a UV detector set at 220 nm. Unless otherwise stated, purifications were done on 40-63 mesh silica gel columns, or using a BIOTAGE® Horizon system, or using specified HPLC equipment and conditions.

Step 1:

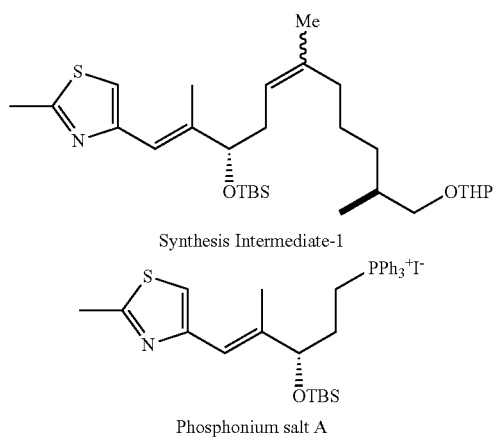

Synthesis Intermediate-1

Phosphonium salt A

To a solution of phosphonium salt A (prepared according to Nicolaou et al., *J. Am. Chem. Soc.*, 119:7974-7991 (1997); 40.5 g, 57.9 mmol) in 300 mL THF at 0° was added sodium bis(trimethylsilyl)amide (63.7 mL, 63.7 mmol), and the solution was stirred for 5 min. A solution of (6S)-6-methyl-7-(tetrahydro-2H-pyran-2-yloxy)heptan-2-one (prepared according to U.S. Pat. No. 7,326,798; 14.54 g, 63.7 mmol) in 50 mL of THF was added rapidly, and the mixture was allowed to warm to RT over 16 h. The reaction mixture was poured into saturated NH$_4$Cl, and extracted with EtOAc (300 mL). The organic layer was washed with brine, dried over magnesium sulfate, filtered, and evaporated in vacuo. The crude product was purified on a silica gel column (EtOAc/hexane 0-10%) to yield 16 g (30.7 mmol, 53%) of Synthesis Intermediate-1. $^1$H NMR (500 MHz, CDCl$_3$) δ ppm 6.90 (s, 1H), 6.43 (s, 1H). 5.20-5.05 (m, 1H), 4.6-4.5 (m, 1H), 4.15-4.00 (m, 1H), 3.9-3.8 (m, 1H), 3.6-3.3 (m, 2H), 3.25-3.05 (m, 1H), 2.70 (s, 3H), 2.35-2.15 (m, 2H), 2.05-1.90 (m, 5H), 1.90-1.75 (m, 1H), 1.75-1.65 (m, 3H), 1.65-1.45 (m, 6H), 1.45-1.25 (m, 3H), 1.15-1.00 (m, 1H), 1.00-0.80 (m, 12H), 0.05--0.05 (dd, 6H). MS (LCMS) [M+H]=522.44, [M+Na]=544.42.

Step 2:

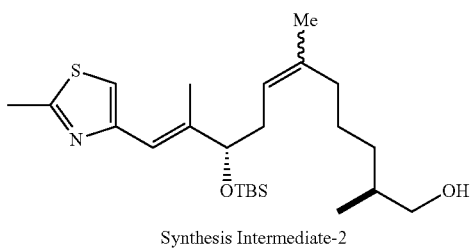

Synthesis Intermediate-2

To a solution of Synthesis Intermediate-1 (16 g, 30.7 mmol) in 300 mL of ethanol at RT was added p-toluenesulfonic acid monohydrate (5.83 g, 30.7 mmol). The mixture was stirred for 7 h, poured into saturated NaHCO$_3$ and extracted twice with methylene chloride (300 mL). The combined organic layers were washed with brine and dried over magnesium sulfate. After filtration and removal of the solvent, the crude material was purified using a BIOTAGE® system (EtOAc/hexane, 10-45%) to yield 9.8 g (22.4 mmol, 73%) of Synthesis Intermediate-2. $^1$H NMR (500 MHz, CDCl$_3$) δ ppm 6.92-6.90 (m, 1H), 6.45-6.40 (m, 1H), 5.15-5.00 (m, 1H), 4.10-4.00 (m, 1H), 3.50-3.30 (m, 2H), 2.69 (s, 3H), 2.35-2.15 (m, 2H), 2.1-1.9 (m, 5H), 1.75-1.50 (m, 5H), 1.50-1.25 (m, 3H), 1.10-0.75 (m, 13H), 0.05--0.05 (dd, 6H). MS (LCMS) [M+H]=438.29, [M+Na]=460.24.

Step 3:

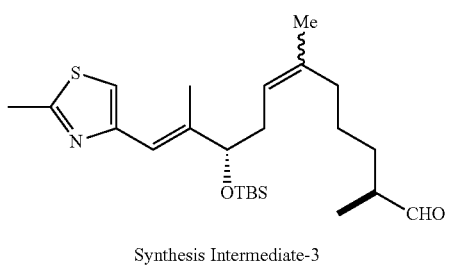

Synthesis Intermediate-3

To a solution of oxalyl chloride (2.94 mL, 33.6 mmol) in 100 mL of methylene chloride was added DMSO (4.88 mL, 68.8 mmol) slowly at −78°. After stirring 10 minutes, Synthesis Intermediate-2 (7 g, 15.99 mmol) in 100 mL methylene chloride was added and stirring was continued for 30 min. TEA (11.14 mL, 80 mmol) was added, and the mixture was allowed to warm to −10°. After saturated NaHCO$_3$ was added, the reaction mixture was extracted twice with methylene chloride (100 mL). The combined organic layers were washed with brine, dried over Na$_2$SO$_4$, filtered and evaporated to give the crude product as a yellow oil. Filtration through a short SiO$_2$ column, eluting with 15% EtOAc/hexane solvent, and concentration in vacuo provided 7 g (16 mmol, 100%) of Synthesis Intermediate-3 as a colorless oil. $^1$H NMR (500 MHz, CDCl$_3$) δ ppm 9.6-9.5 (d, 1H), 6.9 (m, 1H). 6.4 (m, 1H), 5.2-5.1 (m, 1H), 4.1-4.0 (m, 1H), 2.7 (s, 3H), 2.3-2.2 (m, 3H), 2.2-1.8 (m, 5H), 1.7-1.5 (m, 4H), 1.4-1.2 (m, 3H), 1.1-1.0 (m, 3H), 0.87 (s, 9H), 0.03 (s, 3H), 0.01 (s, 3H).

Step 4:

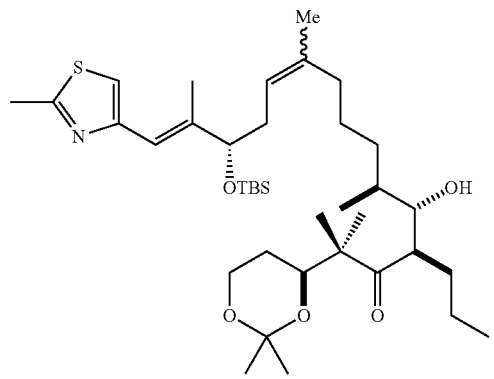

Synthesis Intermediate-4

The method of Klar et al. (*Angew. Chem. Int. Ed.*, 45:7942-7948 (2006)) was followed. To 200 mL of THF at −78° was added 70 mL of 0.5M freshly prepared LDA (35 mmol), followed by 8.48 g (35 mmol) of (S)-2-(2,2-dimethyl-1,3-dioxan-4-yl)-2-methylheptan-3-one (Klar et al., *Synthesis*, 2:301-305 (2005)). Stirring was continued for 30 min at −30°. After cooling to −78°, a solution of 1.0M ZnCl$_2$ (35.0 mL, 35 mmol) was added, and the resulting solution was stirred for 20 min. A solution of Synthesis Intermediate-3 (7 g, 16.06 mmol) in 50 mL of THF was added over 20 min. The mixture was stirred for an additional 8 h at −78°. The mixture was poured into saturated NH$_4$Cl and extracted twice with EtOAc (300 mL). The organic layers were washed with brine, dried over Na₂SO₄ and concentrated in vacuo. The residue was purified using a SiO₂ column (EtOAc/hexane, 0-10%) to provide 7.5 g (11 mmol, 69%) of Synthesis Intermediate-4 as the first eluting and major aldol isomer. ¹H NMR (500 MHz, CDCl₃) δ ppm 6.90 (m, 1H), 6.43 (m, 1H), 5.15-5.05 (m, 1H), 4.15-4.00 (m, 2H), 4.00-3.80 (m, 2H), 3.50-3.40 (m, 1H), 3.30-3.20 (m, 1H), 2.85-2.75 (m 1H), 2.69 (s, 3H), 2.35-2.15 (m, 2H), 2.10-1.90 (m, 5H), 1.75-0.75 (m, 41H), 0.05--0.05 (d, 6H). MS (LCMS) [M+H]=678.47, [M+Na]=700.44.

Step 5:

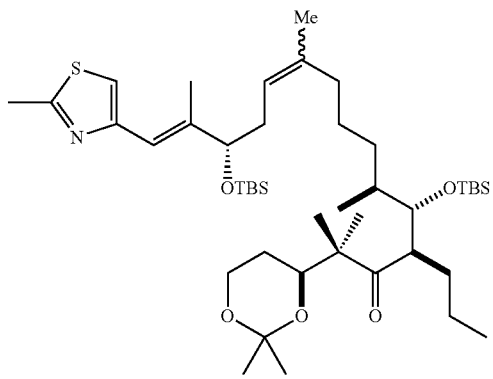

Synthesis Intermediate-5

To a solution of Synthesis Intermediate-4 (8 g, 11.8 mmol) in 200 mL of methylene chloride at 0° was added 2,6-lutidine (6.87 mL, 59 mmol), followed by tert-butyldimethylsilyl trifluoromethanesulfonate (8.13 mL, 35.4 mmol). The mixture was allowed to warm to RT over 16 h, poured into saturated NaHCO₃ and extracted with methylene chloride. The organic layers were washed with brine, dried over Na₂SO₄ and the solvents were removed in vacuo. The residue was purified on a SiO₂ column (EtOAc/hexane, 5-10%) to yield Synthesis Intermediate-5 (7.8 g, 9.84 mmol, 83%). ¹H NMR (500 MHz, CDCl₃) δ ppm 6.90 (s, 1H), 6.44 (s, 1H), 5.15-5.05 (m, 1H), 4.25-4.20 (m, 1H), 4.10-4.00 (m, 1H), 4.00-3.90 (m, 1H), 3.90-3.75 (m, 1H), 3.75-3.70 (m, 1H), 3.10-3.00 (, 1H), 2.70 (s, 3H), 2.35-2.15 (m, 2H), 2.00-1.85 (m, 5H), 1.70-0.75 (m, 50H), 0.10--0.05 (m, 12H). MS (LCMS) [M+H]=792.48, [M+Na]=814.44.

Step 6:

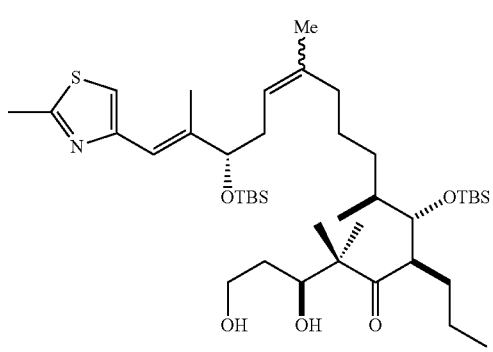

Synthesis Intermediate-6

To a solution of Synthesis Intermediate-5 (6.8 g, 8.58 mmol) in 100 mL of ethanol at RT was added p-toluenesulfonic acid monohydrate (1.8 g, 9.44 mmol). After stirring for 6 h, saturated NaHCO₃ was added and the mixture was extracted with EtOAc. The organic layers were washed with brine, dried over Na₂SO₄ and concentrated in vacuo. The reaction was repeated using 1 g of Synthesis Intermediate-5. The combined crude products were purified using a BIOTAGE® system (EtOAc/hexane, 10-40%) to yield Synthesis Intermediate-6 (5 g, 6.65 mmol, 68%). ¹H NMR (500 MHz, CDCl₃) δ ppm 6.9 (s, 1H), 6.44 (s, 1H), 5.15-5.05 (m, 1H), 4.15-4.00 (m, 1H), 4.00-3.90 (m, 1H), 3.90-3.80 (m, 1H), 3.75-3.65 (m, 1H), 3.65-3.55 (m, 1H), 3.10-2.90 (m, 2H), 2.69 (s, 3H), 2.25-2.15 (m, 2H), 2.00-0.75 (m, 50H), 0.10--0.05 (m, 12H). MS (LCMS) [M+H]=752.42.

Step 7:

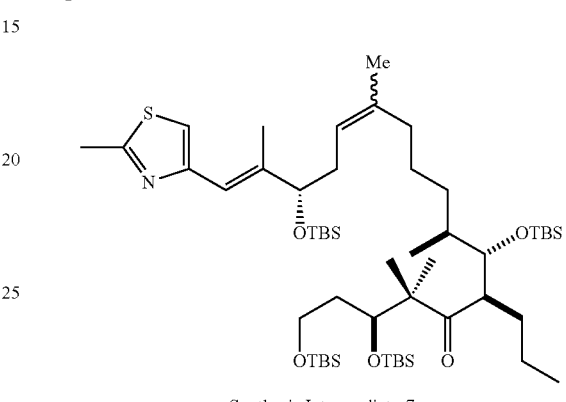

Synthesis Intermediate-7

To a solution of Synthesis Intermediate-6 (5 g, 6.65 mmol) in 200 mL of methylene chloride at 0° was added 2,6-lutidine (7.7 mL, 66.5 mmol), followed by tert-butyldimethylsilyl trifluoromethanesulfonate (9.16 mL, 39.9 mmol). The mixture was allowed to warm to RT over 16 h, then poured into saturated NaHCO₃ and extracted with methylene chloride. The organic solvent was evaporated and the crude mixture was filtered through a layer of SiO₂ with EtOAc/hexane (10-20%) to provide Synthesis Intermediate-7 as an oil (6.9 g, 100%). ¹H NMR (500 MHz, CDCl₃) δ ppm 6.9 (s, 1H), 6.44 (s, 1H), 5.20-5.05 (m, 1H), 4.10-4.00 (m, 1H), 3.95-3.85 (m, 1H), 3.80-3.75 (m, 1H), 3.70-3.60 (m, 1H), 3.60-3.50 (m, 1H), 3.10-3.00 (m, 1H), 2.69 (s, 3H), 2.25-2.15 (m, 2H), 2.00-0.75 (m, 67H), 0.10--0.05 (m, 24H).

Step 8:

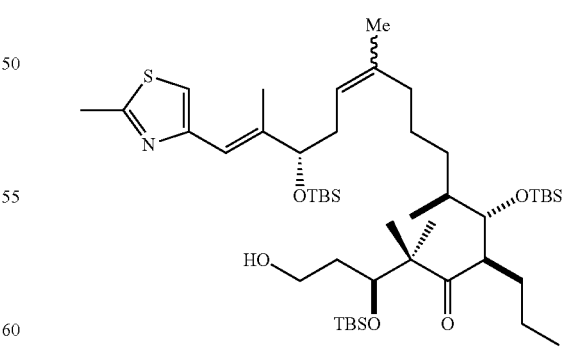

Synthesis Intermediate-8

To a solution of Synthesis Intermediate-7 (5 g, 5.1 mmol) in 80 mL of methylene chloride and 40 mL of MeOH at 0° was added (+/−)-camphor-10-sulfonic acid (1.18 g, 5.1 mmol). The mixture was stirred for 6 h at 0°, poured into saturated NaHCO$_3$ and extracted with methylene chloride. The organic layers were washed with brine, dried over Na$_2$SO$_4$ and concentrated to yield Synthesis Intermediate-8 as an oil (3.6 g, 4.15 mmol, 81%). $^1$H NMR (500 MHz, CDCl$_3$) δ ppm 6.90 (s, 1H), 6.44 (s, 1H), 5.2-5.1 (m, 1H), 4.1-4.0 (m, 2H), 3.85-3.75 (m, 1H), 3.7-3.6 (m, 2H), 3.1-3.0 (m, 1H), 2.7 (s, 3H), 2.3-2.2 (m, 2H), 2.0-1.9 (m, 6H), 1.7-1.5 (m, 5H), 1.5-1.3 (m, 3H), 1.3-1.1 (m, 6H), 1.1-1.0 (m, 4H), 1.0-0.8 (m, 35H), 0.1--0.1 (m, 18H). MS (LCMS) [M+H]=866.49.

Step 9:

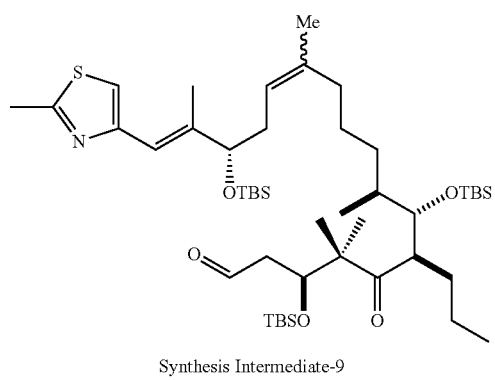

Synthesis Intermediate-9

To a solution of oxalyl chloride (0.8 mL, 9.14 mmol) in 40 mL of methylene chloride at −78° was added DMSO (1.24 mL, 17.5 mmol). After stirring for 10 min, a solution of Synthesis Intermediate-8 (3.6 g, 4.15 mmol) in 40 mL of methylene chloride was added. After 30 min, TEA (3.76 mL, 27.0 mmol) was added and the reaction mixture was allowed to warm to 0° over 2 h. Saturated NaHCO$_3$ was added and the mixture was extracted with methylene chloride. The organic layers were washed with brine, dried over Na$_2$SO$_4$ and concentrated in vacuo to provide Synthesis Intermediate-9 as an oil (3.6 g, 4.16 mmol, 100%). $^1$H NMR (500 MHz, CDCl$_3$) δ ppm 9.77 (m, 1H), 6.9 (s, 1H), 6.44 (s, 1H), 5.3 (s, 1H), 5.2-5.1 (m, 1H), 4.5-4.4 (m, 1H), 4.1-4.0 (m, 1H), 3.8-3.7 (m, 1H), 3.1-3.0 (m, 1H), 2.7 (s, 3H), 2.6-2.1 (m, 4H), 2.0-1.9 (m, 4H), 1.7-1.5 (m, 4H), 1.5-1.3 (m, 5H), 1.3-1.1 (m, 5H), 1.1-1.0 (m, 3H), 1.0-0.8 (m, 35H), 0.1--0.1 (m, 18H).

Step 10:

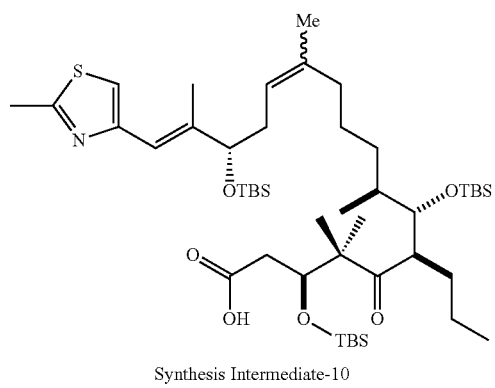

Synthesis Intermediate-10

To a solution of Synthesis Intermediate-9 (3.6 g, 4.16 mmol) in 120 mL of t-BuOH and 85 mL of THF at 0° was added 30 mL of water, 2-methylbut-1-ene (18.5 g, 264 mmol), sodium dihydrogenphosphate (1.6 g, 13.2 mmol) and sodium chlorite (2.98 g, 26.4 mmol). After stirring 2 h at 0°, the mixture was poured into saturated Na$_2$S$_2$O$_3$ solution (100 mL) and extracted three times with EtOAc (300 mL). The combined organic layers were washed with brine, dried over Na$_2$SO$_4$, and concentrated in vacuo. The residue was purified using a BIOTAGE® system (EtOAc/hexane, 10-50%) to give Synthesis Intermediate-10 as a colorless oil (2.8 g, 3.18 mmol, 72%). $^1$H NMR (500 MHz, CDCl$_3$) δ ppm 6.93 (s, 1H), 6.66 (s, 0.5H), 6.46 (s, 0.5H), 5.25-5.0 (m, 1H), 4.4-4.3 (m, 1H), 4.2-4.0 (m, 1H), 3.9-3.7 (m, 1H), 3.2-3.0 (m, 1H), 2.7 (d, 3H), 2.6-2.4 (m, 1H), 2.4-2.0 (m, 3H), 2.0-1.0 (m, 23H), 1.0-0.8 (m, 35H), 0.1--0.1 (m, 18H). MS (LCMS) [M+H]=881.53.

Step 11:

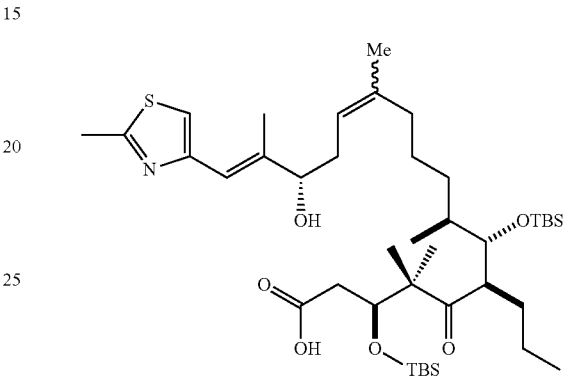

Synthesis Intermediate-11

To a solution of Synthesis Intermediate-10 (2.8 g, 3.18 mmol) in 5 mL of THF at RT was added TBAF (42 mL, 1.0M). The mixture was stirred for 6 h, then poured into saturated NH$_4$Cl, and extracted twice with EtOAc (300 mL). The combined organic layers were washed with HCl (1.0 N, 200 mL), saturated NaHCO$_3$ and brine, and dried over Na$_2$SO$_4$ to give Synthesis Intermediate-11 as a viscous oil (2.6 g, 3.3 mmol, 100%). $^1$H NMR (500 MHz, CDCl$_3$) δ ppm 6.9 (s, 1H), 6.6-6.5 (m, 1H), 5.2-5.1 (m, 1H), 4.4-4.3 (m, 1H), 4.15-4.05 (m, 1H), 3.8-3.7 (m, 1H), 3.4-3.2 (m, 1H), 3.1-3.0 (m, 1H), 2.8-2.7 (m, 2H), 2.66 (d, 3H), 2.5-2.4 (m, 1H), 2.4-2.3 (m, 2H), 2.3-2.2 (m, 1H), 2.0-0.8 (m, 46H), 0.1-0.0 (m, 12H). MS (LCMS) [M+H]=766.3, [M−H$_2$O]=748.3.

Step 12:

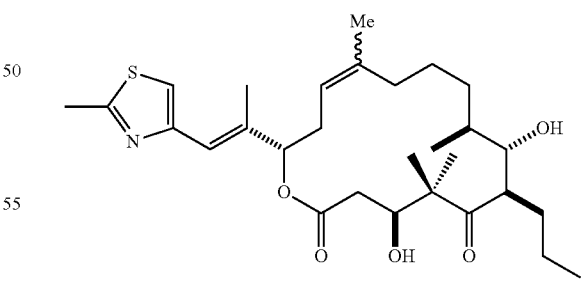

13 E/Z Mixture of Compound III

To a solution of Synthesis Intermediate-11 (2.6 g, 3.3 mmol) in 27 mL of THF at RT was added TEA (2.36 mL, 17 mmol), followed by 2,4,6-trichlorobenzoyl chloride (3.31 g, 13.57 mmol). The reaction mixture was stirred for 20 min, then diluted with 260 mL of toluene. The toluene solution was added slowly to a stirred mixture of DMAP (3.86 g, 31.6 mmol) in 1400 mL toluene over 4 h, after which TLC indicated completion. HCl (4.0N, 12.5 mL) was added, and the solvent was removed in vacuo. The residue was partially purified using a BIOTAGE® system (EtOAc/hexane, 0-10%), providing a mixture which contained a mono-silyl product and the above mixture (13 E/Z isomers) including Compound III (1.1 g). MS (LCMS) (520.2, 634.2). This material was subjected to deprotection without further purification.

Step 13: Compound III

To a solution of the reaction mixture above (102 mg) at −20° was added 1 mL of TFA/CH$_2$Cl$_2$ (20% v/v). The reaction mixture was transferred to an ice bath and stirred for 1 h. The solvent was removed in vacuo, adding small portions of toluene then re-evaporating, which provided a white solid. The same reaction was repeated with 125 mg of the partially purified mixture. The two reaction residues were combined and purified on a SiO$_2$ column (EtOAc/hexane, 20-35%) which provided a white solid (180 mg). The white solid was taken up in 5 mL of MeOH, and purified by HPLC (Varian, Dynamax PDA-2 detector; Waters C18 column; A: water with 0.05% TFA; B: acetonitrile with 0.05% TFA, isocratic). Two major peaks were collected (Peak 1, 73.4 mg, 38%; and Peak 2, 41.8 mg, 22%).

Peak 1 was determined to be the 13-Z (1-oxa numbering) isomer by observation of NOE between the C-14 olefinic proton and the C-13 methyl. $^1$H NMR (500 MHz, CDCl$_3$) δ ppm 7.14 (s, 1H), 6.75 (s, 1H), 5.15-5.05 (m, 1H), 5.05-5.00 (m, 1H), 4.45-4.35 (m, 1H), 3.65-3.55 (m, 1H), 3.35-3.25 (m, 1H), 2.92 (s, 3H), 2.55-2.45 (m, 2H), 2.35-2.25 (m, 2H), 2.25-2.15 (m, 1H), 2.00 (s, 3H), 1.90-1.80 (m, 1H), 1.80-1.65 (m, 5H), 1.60-1.45 (m, 2H), 1.45-1.30 (m, 5H), 1.25-1.15 (m, 3H), 1.05-0.95 (m, 6H), 0.90-0.85 (t, 3H). MS (LCMS) [M+H]=520.3.

Peak 2 was determined to be the 13-E isomer (Compound III for Example 7 experiment, below) by absence of NOE between the C-14 olefinic proton and the C-13 methyl. $^1$H NMR (500 MHz, CDCl$_3$) δ ppm 7.03 (s, 1H), 6.65 (s, 1H), 5.3-5.2 (m, 1H), 5.05-5.00 (m, 1H), 4.45-4.40 (m, 1H), 3.65-3.60 (m, 1H), 3.4-3.3 (m, 1H), 2.77 (s, 3H), 2.6-2.3 (m, 4H), 2.15-2.05 (m, 1H), 1.99 (s, 3H), 1.95-1.85 (m, 1H), 1.8-1.7 (m, 2H), 1.57 (s, 3H), 1.50-1.35 (m, 4H), 1.29 (s, 3H), 1.25-1.10 (m, 3H), 1.0-0.9 (m, 6H), 0.9-0.8 (t, 3H). MS (LCMS) [M+H]=520.3.

Oral In-Vivo Studies with Epothilone D and Compound III

For each compound (epothilone D and Compound III, prepared and described as per the experiment immediately above), three mice per group (10 mpk and 35 mpk) were dosed at 10 ml/kg using 85% PEG-400, 10% TPGS, and 5.0% ethanol. At various intervals after dosing, the plasma, brain, and liver compound levels were measured following tissue homogenization, extraction with acetonitrile, and liquid chromatography with tandem mass spectrometry (LC/MS/MS). Results from the studies are summarized in Tables 4 and 5 and also, the results of the 35 mpk study are reported in FIG. 9. Specifically, Table 4 reports the concentration of epothilone D (Compound 1) and Compound III in the brain after oral administration (10 mpk) up to 24 h after dosing (for Compound III, to the extent still detectible given LLQ), and Table 5 reports and FIG. 9 plots, the concentration of epothilone D (Compound 1) and Compound III in the brain after oral administration (35 mpk) up to 5 to 24 h after dosing (again, for Compound III, to the extent detectible). (A plot was not prepared for the Table 4 data as only one brain concentration value was detectible for Compound III.) In Tables 4 and 5, below, where the values were <LLQ, the LLQ value is noted in the parenthetical.

TABLE 4

| Compound | Time (hr) | Plasma conc (nM) | Brain conc (nM) | Brain/Plasma Ratio | Brain/Liver Ratio |
|---|---|---|---|---|---|
| Compound III | 1 | 12.3 | 9.6 | 0.8 | 0.1 |
| | 5 | 1.3 | <LLQ (3.7 nM) | NQ | NQ |
| | 7 | 1.2 | <LLQ (3.7 nM) | NQ | NQ |
| | 24 | <LLQ (0.2 nM) | <LLQ (3.7 nM) | NQ | NQ |
| Epothilone D | 1 | 15.1 | 10.6 | 0.7 | 0.4 |
| | 3 | 3.9 | 7.0 | 1.8 | 1.3 |
| | 4 | 2.5 | 9.9 | 4.0 | 3.4 |
| | 8 | 1.4 | 6.4 | 4.6 | 1.8 |
| | 13 | 0.1 | 6.3 | 47.3 | 5.1 |
| | 24 | 0.2 | 9.1 | 44.5 | 8.0 |
| | 48 | <LLQ (0.1 nM) | 5.4 | NQ | NQ |
| | 96 | <LLQ (0.1 nM) | 3.0 | NQ | NQ |

TABLE 5

| Compound | Time (hr) | Plasma conc (nM) | Brain conc (nM) | Brain/Plasma Ratio | Brain/Liver Ratio |
|---|---|---|---|---|---|
| Compound III | 1 | 47.7 | 67.7 | 2.3 | 0.4 |
| | 5 | 3.0 | 4.6 | 1.4 | NQ |
| | 24 | 0.7 | <LLQ | NQ | NQ |
| Epothilone D | 1 | 52.7 | 61.3 | 1.1 | 0.5 |
| | 5 | 3.6 | 76.9 | 25.2 | 11.3 |
| | 24 | <LLQ (0.5 nM) | 118 | NQ | 18.7 |

As can be seen, for Compound III, tissue levels from later times (i.e., after 1 h or more) show that Compound III levels decreased rapidly in brain tissue. Hence, Compound III has poor brain retention as observed in the lack of measureable brain levels at 24 h in both experiments. Oral dosing with epothilone D revealed brain-to-plasma ratios of 0.7 and 1.1 at 1 hour, reflecting good brain penetrance. Unlike Compound III, brain levels of epothilone D were maintained for more than 24 h (Tables 2, 4 and 5, FIGS. 9-10). The brain-to-liver ratio for oral dosing of epothilone D indicates that epothilone D is selectively retained in the brain, consistent with the data in Tables 1 and 2 after IV dosing. In particular, the brain-to-liver ratio for epothilone D was 8 and 19 at 24 h after dosing at 10 mpk and 35 mpk, respectively (Tables 4 and 5). These values reflect remarkably high selective brain-to-liver retention rates for epothilone D.

Example 8

Epothilone D Half-Life Data Following IV, Oral, and IP Administration

To further evaluate epothilone D's properties for treating tauopathies, the brain half-life of epothilone D was calculated from multiple studies, and the results are reported in Table 6. To calculate an accurate brain half-life for a long half-life compound, measurements need to be taken for several half lives after a single dose. From the study described in Table 2, where brain concentrations were measured through 7 days after a single dose, the brain half life of epothilone D (Compound I) after IV dosing is 61 h (Table 6). The brain half life in mice after multiple routes of administration and dosages averaged 46.0+/−7 h (Table 6). Similarly, the brain half-life after IV dosing in rats was 31 h (Table 6). In contrast, the brain half life of Compound III was clearly significantly shorter than epothilone D, as reflected in FIG. 9. As a further illustration of the epothilone D brain half-life, FIG. 10 is provided which plots the results of a study (data reported in Table 2, above), showing brain concentration levels at time periods of up to 175 h post-dosing, following a 5 mpk bolus IV administration.

TABLE 6

| Species | Route | Dose (mpk) | Half life (hours) |
|---|---|---|---|
| Mouse | IV | 5 | 61 |
| Mouse | Oral | 10 | 46 |
| Mouse | IP | 1 | 44 |
|  | IP | 10 | 41, 37, 45, 46 |
| Rat | IV | 1 | 31 |

LIST OF CITATIONS

Altmann et al., "The Chemistry and Biology of Epothilones—The Wheel Keeps Turning", Chem. Med. Chem., Vol. 2 (2007).

Andorfer, C. et al., "Cell-cycle reentry and cell death in transgenic mice expressing nonmutant human tau isoforms", J. Neurosci., 25(22):5446-5454 (2005).

Andrieux, A. et al., "Microtubule stabilizer ameliorates synaptic function and behavior in a mouse model for schizophrenia", Biol. Psychiatry, 60(11):1224-1230 (2006).

Avila, J. et al., "Role of tau protein in both physiological and pathological conditions", Physiol. Rev., 84(2):361-384 (2004).

Ballatore, C. et al., "Paclitaxel C-10 carbamates: potential candidates for the treatment of neurodegenerative tauopathies", Bioorg. Med. Chem. Lett., 17(13):3642-3646 (2007).

Bartosik-Psujek, H. et al., "The CSF levels of total-tau and phosphotau in patients with relapsing-remitting multiple sclerosis", J. Neural. Transm., 113(3):339-345 (2006).

Berger, Z. et al., "Accumulation of pathological tau species and memory loss in a conditional model of tauopathy", J. Neurosci., 27(14):3650-3662 (2007).

Bergstralh, D. T. et al., "Microtubule stabilizing agents: their molecular signaling consequences and the potential for enhancement by drug combination", Cancer Treat. Rev., 32(3):166-179 (2006).

Bollag, D. M. et al., "Epothilones, a new class of microtubule-stabilizing agents with a taxol-like mechanism of action", Cancer Res., 55(11):2325-2333 (1995).

Burke, W. J. et al., "Taxol protects against calcium-mediated death of differentiated rat pheochromocytoma cells", Life Sci., 55(16):313-319 (1994).

Butler, D. et al., "Microtubule-stabilizing agent prevents protein accumulation-induced loss of synaptic markers", Eur. J. Pharmacol., 562(1-2):20-27 (2007).

Chou, T. C. et al., "Desoxyepothilone B: An efficacious microtubule-targeted antitumor agent with a promising in vivo profile relative to epothilone B", Proc. Natl. Acad. Sci. USA, 95:9642-9647 (1998).

Dickey, C. A. et al., "Current strategies for the treatment of Alzheimer's disease and other tauopathies", Expert Opin. Ther. Targets, 10(5):665-676 (2006).

Divinski, I. et al., "Peptide neuroprotection through specific interaction with brain tubulin", J. Neurochem., 98(3):973-984 (2006).

Fellner, S. et al., "Transport of paclitaxel (Taxol) across the blood-brain barrier in vitro and in vivo", J. Clin. Invest., 110(9):1309-1318 (2002).

Furukawa, K. et al., "Taxol stabilizes [Ca2+]i and protects hippocampal neurons against excitotoxicity", Brain Res., 689(1):141-146 (1995).

Gerth et al. "Epothilons A and B: Antifungal and Cytotoxic Compounds from Sorangium cellulosum (Myxobacteria)," J. Antibiotics, 49(6):560-563 (June 1996), Goedert, M. et al., "Monoclonal antibody AT8 recognises tau protein phosphorylated at both serine 202 and threonine 205", Neurosci. Leu., 189:167-170 (1995).

Gozes, I., "Activity-dependent neuroprotective protein: from gene to drug candidate", Pharmacol. Ther., 114(2):146-154 (2007).

Gozes, I. et al., "Neurotrophic effects of the peptide NAP: a novel neuroprotective drug candidate", Curr. Alzheimer Res., 3(3):197-199 (2006).

Kolman, A., "Epothilone D (Kosan/Roche)", Curr. Opin. Investig. Drugs, 5(6):657-667 (2004).

Lace, G. L. et al., "A brief history of tau: the evolving view of the microtubule-associated protein tau in neurodegenerative diseases", Clin. Neuropathol., 26(2):43-58 (2007).

Lee et al., "Microtubule stabilizing drugs for the treatment of Alzheimer's disease", Neurobiol. Aging, 15(Supp. 2):S87-S89 (1994).

Magnani, E. et al., "Interaction of tau protein with the dynactin complex", EMBO J., 26(21):4546-4554 (2007).

Matsuoka, Y. et al., "Intranasal NAP administration reduces accumulation of amyloid peptide and tau hyperphosphorylation in a transgenic mouse model of Alzheimer's disease at early pathological stage", J. Mol. Neurosci., 31(2):165-170 (2007).

Matsuoka, Y. et al., "A neuronal microtubule-interacting agent, NAPVSIPQ, reduces tau pathology and enhances cognitive function in a mouse model of Alzheimer's disease", J. Pharmacol. Exp. Ther., 325(1):146-153 (2008).

Michaelis, M. L., "Ongoing in vivo studies with cytoskeletal drugs in tau transgenic mice", Curr. Alzheimer Res., 3(3):215-219 (2006).

Michaelis, M. L. et al., "{beta}-Amyloid-induced neurodegeneration and protection by structurally diverse microtubule-stabilizing agents", J. Pharmacol. Exp. Ther., 312(2):659-668 (2005).

Michaelis, M. L. et al., "Cytoskeletal integrity as a drug target", Curr. Alzheimer Res., 2(2):227-229 (2005).

Minderman, H. et al., "Broad-spectrum modulation of ATP-binding cassette transport proteins by the taxane derivatives ortataxel (IDN-5109, BAY 59-8862) and tRA96023", Cancer Chemother. Pharmacol., 53(5):363-369 (2004).

Moller, A. et al., "Efficient estimation of cell volume and number using the nucleator and the disector", J. Microsc., 159(Pt. 1):61-71(1990).

Morsch, R. et al., "Neurons may live for decades with neurofibrillary tangles", J. Neuropathol. Exp. Neurol., 58(2):188-197 (1999).

Oddo, S. et al., "Triple-transgenic model of Alzheimer's disease with plaques and tangles: intracellular Abeta and synaptic dysfunction", Neuron, 39(3):409-421(2003).

Postma, T. J. et al., "Peripheral neuropathy due to biweekly paclitaxel, epirubicin and cisplatin in patients with advanced ovarian cancer", J. Neuro-Oncology, 45:241-246 (1999).

Preuss, U. et al., "The 'jaws' model of tau-microtubule interaction examined in CHO cells", J. Cell Sci., 110(Pt. 6):789-800 (1997).

Rice, A. et al., "Chemical modification of paclitaxel (Taxol) reduces P-glycoprotein interactions and increases permeation across the blood-brain barrier in vitro and in situ", *J. Med. Chem.*, 48(3):832-838 (2005).

Roberson, E. D. et al., "Reducing endogenous tau ameliorates amyloid beta-induced deficits in an Alzheimer's disease mouse model." *Science*, 316(5825):750-754 (2007).

Roy, S. et al., "Axonal transport defects: a common theme in neurodegenerative diseases", *Acta Neuropathol.*, 109(1):5-13 (2005).

Santacruz, K. et al., "Tau suppression in a neurodegenerative mouse model improves memory function", *Science*, 309 (5733):476-481(2005).

Spittaels, K. et al., "Glycogen synthase kinase-3beta phosphorylates protein tau and rescues the axonopathy in the central nervous system of human four-repeat tau transgenic mice", *J. Biol. Chem.*, 275(52):41340-41349 (2000).

Sponne, I. et al., "Apoptotic neuronal cell death induced by the non-fibrillar amyloid-beta peptide proceeds through an early reactive oxygen species-dependent cytoskeleton perturbation", *J. Biol. Chem.*, 278(5):3437-3445 (2003).

Terwel, D. et al., "Amyloid activates GSK-3beta to aggravate neuronal tauopathy in bigenic mice", *Am. J. Pathol.*, 172 (3):786-798 (2008).

Wagner, B. K et al., "Large-scale chemical dissection of mitochondrial function", *Nat. Biotech.*, 26(3):343-351 (2008).

Wostyn, P. et al., "Alzheimer's disease-related changes in diseases characterized by elevation of intracranial or intraocular pressure", *Clin. Neurol. Neurosurg.*, 110(2):101-109 (2008).

Zhang, B. et al., "Microtubule-binding drugs offset tau sequestration by stabilizing microtubules and reversing fast axonal transport deficits in a tauopathy model", *Proc. Natl. Acad. Sci. USA*, 102(1):227-231(2005).

We claim:

1. A method of treating Alzheimer's Disease comprising administering a therapeutically-effective amount of epothilone D to a patient in need of treatment thereof, wherein the cumulative monthly dose of epothilone D administered to the patient is from about 0.01 mg/m$^2$ to about 5 mg/m$^2$.

2. The method of claim 1, wherein the epothilone D is administered orally.

3. The method of claim 1, wherein the epothilone D is administered intravenously.

4. The method of claim 1, wherein the epothilone D has brain penetrance of 0.5 or more measured at a period between 20 minutes and 1 hour post-dosing, and either or both of 1) a brain half-life of 24 hours or more, and 2) brain to liver selective retention of 2 or more at 24 or more hours post-dosing.

5. The method of claim 1, wherein the method is therapeutically effective in treating Alzheimer's Disease in the patient without causing drug-induced side effects that would require that use of the epothilone D treatment be discontinued.

6. The method of claim 1, wherein the epothilone D is administered intravenously to a human patient.

7. A method of treating Alzheimer's Disease in a human patient, comprising the step of administering a therapeutically effective amount of epothilone D to the patient, wherein the epothilone D is administered according to a dosing regime that provides a cumulative monthly dose of epothilone D to the patient of from about 0.01 mg/m$^2$ to about 5 mg/m$^2$ and wherein the epothilone D is therapeutically effective in having an impact on underlying disease and/or providing cognitive benefits to the patient without causing drug-induced side effects that would require that use of the epothilone D treatment be discontinued.

8. The method of claim 7, wherein the epothilone D is administered intravenously to the human patient.

* * * * *